(12) United States Patent
Ellsworth et al.

(10) Patent No.: US 10,757,945 B2
(45) Date of Patent: Sep. 1, 2020

(54) OZONE TREATMENT FOR ELIMINATION OF PATHOGENS

(71) Applicant: WillowPure, LLC, Denver, CO (US)

(72) Inventors: Jill Lynn Ellsworth, Aurora, CO (US); Jason R. Ellsworth, Aurora, CO (US)

(73) Assignee: WillowPure, LLC, Denver, CO (US)

( * ) Notice: Subject to any disclaimer, the term of this patent is extended or adjusted under 35 U.S.C. 154(b) by 0 days.

(21) Appl. No.: 16/675,966

(22) Filed: Nov. 6, 2019

(65) Prior Publication Data

US 2020/0068899 A1 Mar. 5, 2020

Related U.S. Application Data

(63) Continuation of application No. 15/496,912, filed on Apr. 25, 2017.

(60) Provisional application No. 62/327,651, filed on Apr. 26, 2016.

(51) Int. Cl.
| | | |
|---|---|---|
| A61L 2/10 | (2006.01) | |
| A01N 59/00 | (2006.01) | |
| C01B 13/10 | (2006.01) | |
| A61L 2/20 | (2006.01) | |

(52) U.S. Cl.
CPC .............. *A01N 59/00* (2013.01); *A61L 2/202* (2013.01); *C01B 13/10* (2013.01)

(58) Field of Classification Search
CPC ..................................................... A61L 2/202
See application file for complete search history.

(56) References Cited

U.S. PATENT DOCUMENTS

| | | |
|---|---|---|
| 5,405,631 A | 4/1995 | Rosenthal |
| 6,120,822 A | 9/2000 | Denvir et al. |
| 6,132,629 A | 10/2000 | Boley |
| 6,387,430 B1 | 5/2002 | Gillette et al. |
| 6,455,017 B1 | 9/2002 | Kasling et al. |
| 6,685,549 B2 | 2/2004 | Henry et al. |
| 6,942,834 B2 | 9/2005 | Gutman |
| 8,017,074 B2 | 9/2011 | Arnold et al. |
| 8,062,500 B2 | 11/2011 | Sumita |
| 8,278,628 B2 | 10/2012 | Hamilton |
| 8,349,253 B2 | 1/2013 | Gutman |
| 8,425,837 B2 | 4/2013 | Carbone et al. |
| 8,540,943 B2 | 9/2013 | Kee et al. |
| 8,617,479 B2 | 12/2013 | Gil et al. |
| 8,721,984 B2 | 5/2014 | Carbone et al. |
| 8,754,385 B1 | 6/2014 | Gutman |
| 8,808,622 B2 | 8/2014 | Arnold et al. |
| 9,034,271 B2 | 5/2015 | Shur |
| 9,792,748 B2 | 10/2017 | Campalans et al. |
| 2007/0292305 A1 | 12/2007 | Dempsey |
| 2008/0166263 A1 | 7/2008 | Busted |
| 2009/0252646 A1 | 10/2009 | Holden et al. |
| 2009/0272279 A1 | 11/2009 | Kieck |
| 2009/0274577 A1 | 11/2009 | Sorensen et al. |
| 2009/0304810 A1 | 12/2009 | Martin |
| 2009/0311138 A1 | 12/2009 | Klaptchuk |
| 2010/0192987 A1 | 8/2010 | Steffen |
| 2011/0268850 A1 | 11/2011 | Rasanayagam et al. |
| 2012/0021075 A1 | 1/2012 | Umanskaya et al. |
| 2012/0198870 A1 | 8/2012 | Erbs et al. |
| 2012/0230879 A1 | 9/2012 | Dunkley et al. |
| 2014/0193294 A1 | 7/2014 | Kain |
| 2014/0287068 A1 | 9/2014 | Lewis et al. |
| 2015/0265720 A1* | 9/2015 | Levine ................. A61K 31/352 514/15.2 |
| 2015/0327562 A1 | 11/2015 | Zwijack |
| 2016/0223257 A1* | 8/2016 | Romanek ................. A23B 7/01 |
| 2020/0008428 A1 | 1/2020 | Ellsworth et al. |

FOREIGN PATENT DOCUMENTS

| | | |
|---|---|---|
| WO | WO 2015/175867 | 11/2015 |
| WO | WO 2016/095024 | 6/2016 |

OTHER PUBLICATIONS

Krause et al., "Effects of Ozone on the Sporulation, Germination, and Pathogenicity of Botrytis cinerea," *Physiology and Biochemistry*, vol. 68, pp. 195-198, 1978.

Stopbudrot, "Preventing and Treating Bud Rot—Botrytis," https://stopbudrot.wordpress.com/2014/10/03/preventing-and-treating-bud-rot-botrytis/, Oct. 3, 2014.

"Knock-Out Bugs, Mold, Smells with Ozone," www.mmjdoctoronline.com/health-news/ozone-a-godsend-for-cannabis-cultivators, Feb. 24, 2017.

"The CH-2 ozone CH-3 Ozone Chamber," www.oxidationtech.com/Downloads/ozone_chamber/Brochure-CH-2-OzoneChamber.pdf, Sep. 29, 2017.

"Willow Industries—Cannabis Remediation & Decontamination," web.archive.org/web/20190727140206/https://willowindustries.com/, Jul. 27, 2019.

"Willow Industries—The Data," web.archive.org/web/20190410144158/https://willowindustries.com/the-data/, Apr. 10, 2019.

Calogirou et al., "Decomposition of Terpenes by Ozone during Sampling on Tenax," Anal. Chem., vol. 68, pp. 1499-1506 (1996).

Farre-Armengol et al., "Ozone degrades floral scent and reduces pollinator attraction to flowers," New Phytologist, vol. 209, pp. 152-160 (2016).

Fuentes et al., "Ozone impedes the ability of a herbivore to find its host," Environ. Res. Lett., vol. 8 (5 pages) (2013).

Giese et al., "Development and Validation of a Reliable and Robust Method for the Anlalysis of Cannabinoids and Terpenes in Cannabis," Journal of AOAC International, vol. 98, pp. 1503-1522 (2015).

(Continued)

*Primary Examiner* — Donald R Spamer
(74) *Attorney, Agent, or Firm* — Sonapat LLC

(57) ABSTRACT

The present disclosure relates to the ozone treatment of plants to reduce or eliminate pesticides, mold, yeast, or other pathogens. In an embodiment, the plant is exposed to ozone at a concentration of 150 to 250 ppm for between 15 and 65 minutes. The exposure of the plant to ozone reduces or eliminates pesticides, mold, yeast or other pathogens with little to no negative effects on the plants potency, flavor profile, fragrance, and weight.

20 Claims, 25 Drawing Sheets

(56) References Cited

OTHER PUBLICATIONS

Karaca, "Use of Ozone in the Citrus Industry," Ozone: Science & Engineering, vol. 32, pp. 122-129 (2010).

Krupa et al., "Ambient Ozone and Plant Health," Plant Disease, vol. 85, pp. 4-12 (2001).

Munshi et al., "Rate Constants of the Reactions of Ozone with Nitriles, Acrylates and Terpenes in Gas Phase," Atmospheric Environment, vol. 23, pp. 1971-1976 (1989).

Qiu et al., "Analysis of terpenes and turpentines using gas chromatography with vacuum ultraviolet detection," J. Sep. Sci., vol. 40, pp. 869-877 (2017).

Russo, "Taming THC: potential cannabis synergy and phytocannabinoid-terpenoid entourage effects," British Journal of Pharmacology, vol. 163, pp. 1344-1364 (2011).

Tabakoglu et al., "Enhanced Degradation of Azoxystrobin in Grapes and Model Systems by Ozone Fumigation during Storage," Ozone: Science & Engineering, vol. 37, pp. 479-488 (2015).

Weschler et al., "Indoor ozone/terpene reactions as as source of indoor particles," Atmospheric Environment, vol. 33, pp. 2301-2312 (1999).

420 Magazine, "Ozone: the ultimate decontaminate," from https://www.420magazine.com/community/threads/ozone-the-ultimate-decontaminate.56750/, dated Oct. 3, 2006, printed on Apr. 13, 2020 (13 pages).

International Application No. PCT/US2019/051251, filed Sep. 16, 2019 (75 pages), Willowpure, LLC as Applicant.

\* cited by examiner

| Cannabinoid | Cannabinoid Levels % | mg/gram |
|---|---|---|
| THC | 4.31% | 43.13 |
| THC-A | 72.06% | 720.65 |
| CBD | N/D | N/D |
| CBD-A | N/D | N/D |
| CBN | N/D | N/D |
| CBG | N/D | N/D |
| CBG-A | N/D | N/D |
| CBC | N/D | N/D |
| THCV | N/D | N/D |
| Total | 76.38% | 763.78 |

Cannabinoid Levels

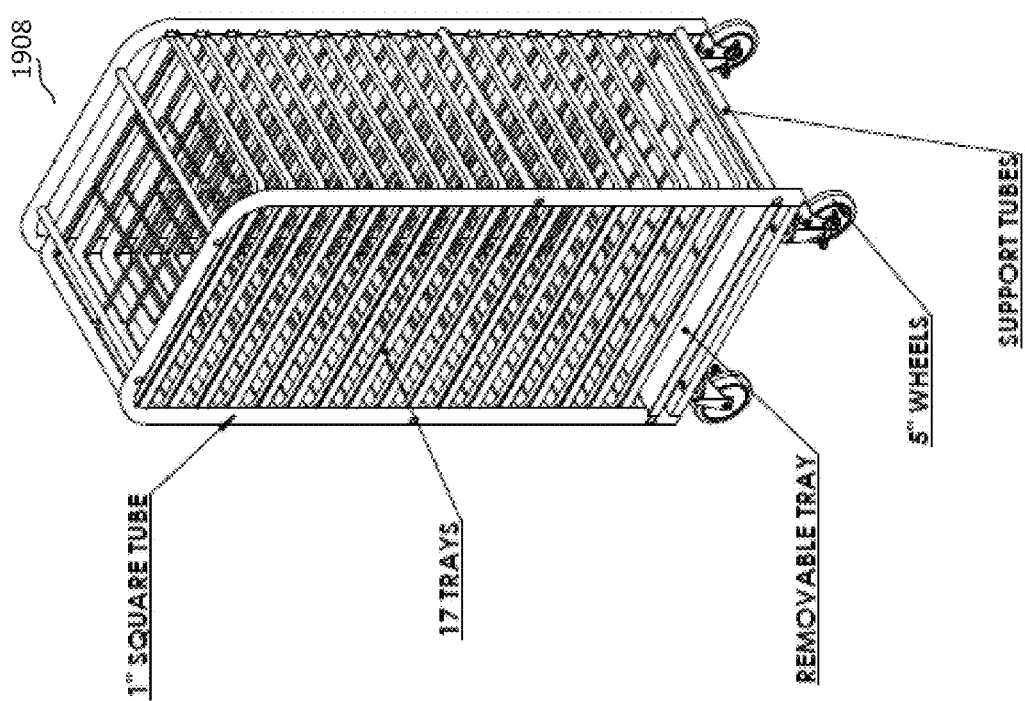

18" W X 25 1/2" L X 1 3/8" D TRAY
MESH REMOVED FOR CLARITY

OZONE TREATMENT FOR ELIMINATION OF PATHOGENS

RELATED APPLICATIONS

This is a continuation of U.S. patent application Ser. No. 15/496,912 filed Apr. 25, 2017, which claims priority to U.S. Provisional Patent Application Ser. No. 62/327,651 filed Apr. 26, 2016, both of which are fully incorporated herein by reference.

INTRODUCTION

The term pesticide covers a wide range of compounds including insecticides, fungicides, herbicides, rodenticides, molluscicides, nematicides, plant growth regulators and others. Pesticides are substances that are used to repel, kill or control animals (insecticides) or plants (herbicides) that are considered to be pests. Currently, the primary method of controlling such pests is through the application of pesticides, which often contain synthetic chemical compounds.

The introduction of synthetic insecticides—organo-phosphate insecticides in the 1960s, carbamates in the 1970s, prethroids in the 1980s and the introduction of herbicides and fungicides in the 1970s and 1980s contributed greatly to pest control and agricultural output. Ideally a pesticide must be lethal to the targeted pests, but not to non-target species, including animals and humans. Unfortunately, this is often not the case.

Despite their agricultural and economic benefits, pesticides can have negative impacts on human health. Many conventional pesticides are synthetic materials that kill or inactivate a pest directly. Short-term exposure to a large amount of certain pesticides can result in serious long-term health detriments and death. Exposure to large amounts of pesticides is usually more likely for people, such as farmers, who may frequently touch and/or breathe in pesticides. Studies have linked the effects of long-term exposure to small amounts of pesticides to a variety of chronic health conditions such as diabetes, cancer and neurological defects, among others.

Studies have shown preliminary evidence that chronic, low-dose exposure to pesticides increases the risk of cognitive impairments and diseases such as Alzheimer's and Parkinson's later in life. A study of 50 pesticides and more than 30,000 licensed pesticide applicators linked exposure of seven pesticides that contain chlorinated compounds (including two herbicides, two organophosphate insecticides and two organochlorines, to increased risk of diabetes). Exposure to pesticides has also been associated with increased infertility in women and developmental problems in children.

The most widely used herbicide in the world, glyphosate, is employed in mass quantities in agriculture around the world. Although glyphosate is thought to be less toxic than many other traditional herbicides, the World Health Organization has announced that it is a probable carcinogen.

In addition to linking herbicides to cancer, plants are known to develop resistance to herbicides over time. Weeds that have developed resistance to one herbicide may require that higher amounts of that herbicides be applied to them to result in sufficient weed suppression and may also require treatment of additional herbicides in a "herbicide cocktail" to keep them under control. Thus, herbicide-tolerant crops will be exposed to higher levels of herbicides as resistance to the most commonly used pesticides increases.

Pesticides have been found to dramatically affect the environment. Pesticides can contaminate soil, water, turf and other vegetation.

Heavy treatment of soil with pesticides can cause populations of beneficial soil microorganisms to decline. Overuse of chemical fertilizer and pesticides have deleterious effects on the soil organisms that are similar to the effects seen by human overuse of antibiotics. Indiscriminate use of chemicals might be useful in the short term, but if used for prolonged periods they can reduce the amount of beneficial nutrient-synthesizing soil organisms to a point where nitrate levels in soil are not sufficient to sustain crops.

Pesticides can reach surface water through runoff from treated plants and soil. Contamination of water by pesticides is widespread. According to one comprehensive set of studies done by the U.S. Geological Survey (USGS) on major river basins across the country in the early to mid-1990s, more than 90 percent of water and fish samples from all streams contained one, or more often, several pesticides. Pesticides were found in all samples from major rivers with mixed agricultural and urban land use influences and 99 percent of samples of urban streams. The USGS also found that concentrations of insecticides in urban streams commonly exceeded guidelines for protection of aquatic life.

Groundwater pollution due to pesticides is a worldwide problem. According to the USGS, at least 143 different pesticides and 21 transformation products have been found in ground water, including pesticides from every major chemical class. Over the past two decades, detections have been found in the ground water of more than 43 states. During one survey, 58 percent of drinking water samples drawn from various hand pumps and wells were contaminated with Organo Chlorine pesticides at levels above EPA safety standards. Once ground water is polluted with toxic chemicals, it may take many years for the contamination to dissipate or be cleaned up. Cleanup may also be very costly and complex, if not impossible.

Although pesticides are often considered a quick, easy and inexpensive solution for controlling weeds, insects, bacteria and other pests, their use comes at a significant cost. Pesticides have contaminated almost every part of the environment. Pesticide residues are found in soil and air, and in surface and ground water everywhere they are used.

Pesticide contamination poses significant risks to the environment including non-target organisms ranging from beneficial soil microorganisms, to insects, plants, fish, birds, and humans.

It is with respect to this general technical environment that aspects of the present technology disclosed herein have been contemplated. Furthermore, although a general environment has been discussed, it should be understood that the examples described herein should not be limited to the general environment identified in the background.

SUMMARY

This summary is provided to introduce a selection of concepts in a simplified form that are further described below in the Detailed Description section. This summary is not intended to identify key features or essential features of the claimed subject matter, nor is it intended to be used as an aid in determining the scope of the claimed subject matter.

In general terms, this disclosure is directed to safely and effectively reducing pathogen levels on plants by exposing plants and their resident pathogens to gaseous ozone. This disclosure is also directed to safely and effectively reducing fungus levels, including yeast and/or mold, on plants by exposing plants and their resident fungus to gaseous ozone. Various aspects are described in this disclosure, which include, but are not limited to, the following aspects and examples.

BRIEF DESCRIPTION OF THE DRAWINGS

Non-limiting examples and non-exhaustive examples are described with reference to the following figures.

FIG. 21C illustrates an off center profile of an embodiment of the pathogen reduction device 1908.

DETAILED DESCRIPTION

Figure 1:
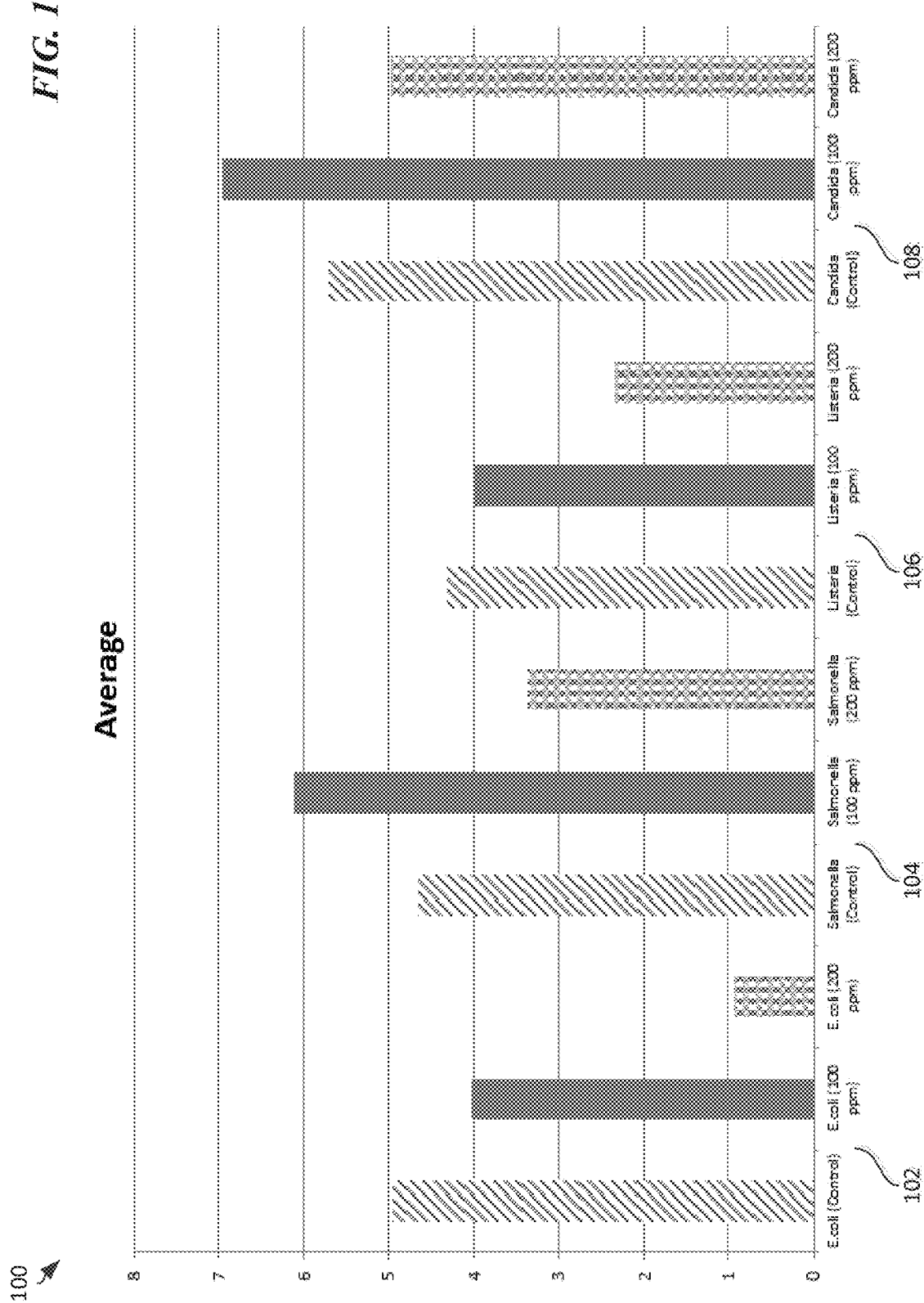
FIG. 1 is a graph showing the average microbial counts from multiple trials after treatment of plant pathogens with gaseous ozone.

Various embodiments will be described in detail with reference to the drawings, wherein like reference numerals represent like parts and assemblies throughout the several views. Additionally, any examples set forth in this specification are not intended to be limiting and merely set forth some of the many possible embodiments in which aspects disclosed herein may be practiced.

As used herein, the recited terms have the following meanings. All other terms and phrases used in this specification, unless otherwise specified, have their ordinary meanings as one of skill in the art would understand after review of this disclosure.

As used herein, "plant" can refer to any portion of a growing plant, including the roots, stems, stalks, leaves, branches, seeds, flowers, fruits, and the like.

As used herein, "pathogen" can refer to anything that causes disease or illness, but especially biological organisms such as bacteria, fungi, and viruses.

As used herein, "pesticide" refers to a composition or product that kills or repels plant or seed pests, and may be broken into any number of particular sub-groups including, but not limited to, acaricides, avicides, bactericides, fungicides, herbicides, insecticides, miticides, molluscicides, nematicides, piscicides, predacides, rodenticides and silvicides. Pesticides may also include chemicals which are not normally used as pest control agents, such as plant growth regulators, defoliants and desiccants, or which are not directly toxic to pests, such as attractants and repellants. Some microbial pesticides may be bacteria, viruses and fungi that cause disease in given species of pests. Pesticides may be organic or inorganic. Pesticides applied to plant seeds may remain on the surface of the seed coat following application, or may absorb into the seed and translocate throughout the plant.

As used herein, "herbicide" refers to a composition or product that kills or deters weed growth. One example of a herbicide includes glyphosate (i.e., RoundUp® herbicide).

As used herein, "insecticide" refers to a composition or product that kills or repels insects. Examples of insecticides include Sevin (carbaryl), permethrin, and *bacillus* thruingiensis.

As used herein, "genetically modified plant" or "genetically modified organism" refers to an organism whose genetic material has been altered using genetic engineering techniques such as recombinant DNA technology.

As used herein, "seed" refers to anything that can be sown to produce a plant. Seed can refer to an unfertilized plant ovule, a fertilized plant ovule, and an embryonic plant. Seed can also refer to a whole or portion of a plant which is sown. For example, seed may refer to a whole or portion of a potato tuber.

As used herein, "applying" refers to bringing one or more components into nearness or contact with another thing or component. Applying can refer to contacting or administering.

As used herein, "fungus" refers to any member of the group of eukaryotic organisms that includes microorganisms such as yeasts and molds.

Aspects of this disclosure relate to a method for reducing plant pathogens comprising: containing one or more of a seed, soil and a plant in a gaseous ozone chamber; concentrating gaseous ozone in the chamber and applying the concentrated gaseous ozone to the one or more of the seed, soil and the plant at a concentration of at least 100 ppm and a temperature in the range of 15° C. to 35° C. for at least 10 minutes.

Additional aspects relate to an ozone treatment system comprising: an oxygen concentrator configured to concentrate oxygen from ambient air; an ozone generator configured to adjust an ozone concentration in an ozone chamber from 0.01 ppm to 500 ppm; one or more processors; and a memory coupled to the one or more processors, the memory for storing instructions which, when executed by the one or more processors, cause the one or more processors to: determine a concentration of gaseous ozone in an ozone chamber; determine an ambient temperature in the ozone chamber; adjust the concentration of gaseous ozone in the ozone chamber to a concentration in the range of 100 ppm to 500 ppm; adjust the ambient temperature in the ozone chamber to a temperature in the range of 15° C. to 35° C.; and continuously monitor the concentration of gaseous ozone and the ambient temperature in the ozone chamber and automatically adjust the monitored concentration and temperature to a preset concentration and a preset temperature.

Other aspects relate to computer-readable media having computer-executable instructions, that when executed by one or more processors perform a method, the method comprising: receiving first data related to a concentration of gaseous ozone in an ozone chamber; receiving second data related to an ambient temperature in the ozone chamber; sending a request to a controller to adjust the concentration of gaseous ozone in the ozone chamber to a concentration in the range of 100 ppm to 500 ppm; and sending a request to the controller to adjust the ambient temperature in the ozone chamber to a temperature in the range of 15° C. to 35° C.

The various embodiments described above are provided by way of illustration only and should not be construed to limit the claims attached hereto. Those skilled in the art will readily recognize various modifications and changes that may be made without following the example embodiments and applications illustrated and described herein, and without departing from the true spirit and scope of the claims.

FIG. 1 is a graph showing average microbial counts from three ozone exposure trials for each of *E. Coli, Salmonella, Listeria*, and *Candida* inoculated *Cannabis* plants. Details regarding that study are as follows.

*Cannabis* plants were individually contaminated with *Escherichia Coli, Salmonella enterica* sv *typhimurium, Listeria monocytogenes* and *Candida albicans* then exposed to gaseous ozone for 20 minutes at 100 ppm and 200 ppm. Significant kills of all bacterial pathogens were observed at 200 ppm while a lesser kill rate was seen at 100 ppm except for the *Escherichia coli* which was observed to be significantly vulnerable to both 100 ppm and 200 ppm concentrations. The effect of ozone treatment on *Candida albicans* were limited; however, testing at ozone concentrations higher than 200 ppm may provide markedly different results, as the results from the 200 ppm trials showed an average reduced microbial count for *Candida albicans* when compared with the control group (see FIG. 10).

Pure cultures of *Escherichia coli* and *Listeria monocytogenes* provided by the American Type Culture Collection (ATCC) were grown in selective media broths. The *Candida albicans* provided by ATCC was grown on potato dextrose agar, and after significant growth was achieved, the colonies were transferred and suspended in Butterfield's buffer. After significant turbidity in each broth of pathogens was observed, they, along with Butterfield's buffer with the suspended *Candida albicans*, were used to inoculate individual *Cannabis* samples. This process created four individual populations of *Cannabis* with each population being contaminated with one of the four organisms grown. After inoculating the samples they were allowed to dry overnight by placing them out in the open at room temperature. Each population of *Cannabis* was then divided into smaller individual 2-4 gram samples which were used in the tests. One test consisted of placing nearly half of the smaller samples into an ozone gas chamber for 20 minutes at an approximate ozone concentration of 100 ppm. The remaining samples were set aside to be used as controls.

Three samples for each organism were tested at each of the concentrations. The control samples were placed into the same chamber for 20 minutes with an ozone concentration of 0 ppm. All samples were then analyzed for their microbial counts by first generating serial dilution using Butterfield's buffer as the diluent for each sample then individually plating the resultant dilutions onto selective media appropriate for the organism being analyzed. After the required incubation temperatures and times were completed, the organisms on the plates were counted. For each set of dilutions of a given sample and starting at the plate representing the lowest dilution ratio, the first plate that was countable was counted and the result was recorded.

Testing occurred over two days. The first day involved testing one sample of *Cannabis* for each organism at an ozone concentration of 100 ppm and another test of only *Listeria* at 50 ppm. Additional testing involving subsequent trials for each organism at ozone concentrations of 100 ppm and 200 ppm were conducted on the second day of testing.

The ozone concentration in the ozone chamber was kept at a range approximating the desired 100 ppm and 200 ppm concentrations. For instance, when the desired concentration was 100 ppm, the actual range of concentrations was 98 ppm to 106 ppm, and when the desired concentration was 200 ppm, the actual range of concentration was 198 ppm to 204 ppm. While the samples were being placed into the chamber ozone gas was lost. It took 3 minutes before the desired concentration of 100 ppm was achieved for tests requiring that ozone concentration and 5 minutes before the desired concentration of 200 ppm was achieved for tests requiring that ozone concentration.

The result of testing can be seen in Table 1 below. At an ozone concentration of 50 ppm, which only *Listeria* was involved with, there was no statistically significant difference between the control and the treated sample. At an ozone concentration of 100 ppm there was a significant kill of all of the organisms involved in the test.

The results of the second day of testing can be seen in Table 2 below. There was a significant kill of all organisms at an ozone concentration of 100 ppm when compared to the controls and at an ozone concentration of 200 ppm the amount of kills increased when compared to the kills at 100 ppm.

TABLE 1

This table shows the concentration range of gaseous ozone present during each test, the amount of time the organisms were subjected to the ozone and the microbial counts after the treatments shown for the first day of testing.

| Microbe | Target Ozone Concentration (ppm) | Actual Ozone Concentration Range (ppm) | Treatment Time (min) | Microbial Count (cfu/g) |
|---|---|---|---|---|
| E. Coli Control | 0 | N/A | 20 | $1.2 * 10^{11}$ |
| E. Coli Treated | 100 | 95-102 | 20 | $2.8 * 10^{10}$ |
| Salmonella Control | 0 | N/A | 20 | $1.1 * 10^{11}$ |
| Salmonella Treated | 100 | 95-102 | 20 | $1.7 * 10^{10}$ |
| Listeria Control | 0 | N/A | 20 | $1.9 * 10^{7}$ |
| Listeria Treated | 100 | 95-102 | 20 | $4.8 * 10^{5}$ |
| Listeria Control | 0 | N/A | 20 | $7.0 * 10^{2}$ |
| Listeria Treated | 50 | 46-52 | 20 | $2.6 * 10^{2}$ |
| Mold Control | 0 | N/A | 20 | $1.4 * 10^{12}$ |
| Mold Treated | 100 | 95-102 | 20 | $1.9 * 10^{11}$ |

TABLE 2

This table shows the concentration range of the gaseous ozone present during each test, the amount of time the organisms were subjected to the ozone and the microbial counts after treatments shown for the second day of testing.

| Microbe | Target Ozone Concentration (ppm) | Actual Ozone Concentration Range (ppm) | Treatment Time (min) | Microbial Count (cfu/g) |
|---|---|---|---|---|
| E. Coli Control | 0 | N/A | 20 | $9.0 * 10^{4}$ |
| E. Coli Trial 1 | 100 | See Table 1 | 20 | See Table 1 |
| E. Coli Trial 2 | 100 | 98-106 | 20 | BLD |
| E. Coli Trial 3 | 100 | 98-106 | 20 | $3.6 * 10^{1}$ |
| E. Coli Trial 1 | 200 | 198-204 | 20 | BLD |
| E. Coli Trial 2 | 200 | 198-204 | 20 | $2.3 * 10^{1}$ |
| E. Coli Trial 3 | 200 | 198-204 | 20 | $2.0 * 10^{1}$ |
| Salmonella Control | 0 | N/A | 20 | $4.5 * 10^{4}$ |
| Salmonella Trial 1 | 100 | 98-106 | 20 | See Table 1 |
| Salmonella Trial 2 | 100 | 98-106 | 20 | $1.1 * 10^{4}$ |
| Salmonella Trial 3 | 100 | See Table 1 | 20 | $1.3 * 10^{4}$ |
| Salmonella Trial 1 | 200 | 198-204 | 20 | $7.0 * 10^{2}$ |
| Salmonella Trial 2 | 200 | 198-204 | 20 | $2.2 * 10^{3}$ |
| Salmonella Trial 3 | 200 | 198-204 | 20 | $8.0 * 10^{3}$ |
| Listeria Control | 0 | N/A | 20 | $2.0 * 10^{4}$ |
| Listeria Trial 1 | 100 | See Table 1 | 20 | See Table 1 |
| Listeria Trial 2 | 100 | 98-106 | 20 | $2.0 * 10^{3}$ |
| Listeria Trial 3 | 100 | 98-106 | 20 | $1.0 * 10^{3}$ |
| Listeria Trial 1 | 200 | 198-204 | 20 | $3.0 * 10^{2}$ |
| Listeria Trial 2 | 200 | 198-204 | 20 | $3.1 * 10^{2}$ |
| Listeria Trial 3 | 200 | 198-204 | 20 | $1.1 * 10^{2}$ |
| Candida Control | 0 | N/A | 20 | $5.0 * 10^{5}$ |
| Candida Trial 1 | 100 | See Table 1 | 20 | See Table 1 |
| Candida Trial 2 | 100 | 98-106 | 20 | $2.7 * 10^{5}$ |
| Candida Trial 3 | 100 | 98-106 | 20 | $1.5 * 10^{4}$ |
| Candida Trial 1 | 200 | 198-204 | 20 | $1.0 * 10^{5}$ |
| Candida Trial 2 | 200 | 198-204 | 20 | $8.3 * 10^{4}$ |
| Candida Trial 3 | 200 | 198-204 | 20 | $9.8 * 10^{4}$ |

"BLD" stands for below the limit of detection.

This study shows that gaseous ozone is an effective antimicrobial step when treating Cannabis samples contaminated with pathogens. It is presumed that plant samples that would be treated for human consumption would not be near the level of contamination that this study generated through the inoculation processes. Therefore the use of gaseous ozone as an antimicrobial step in production would assure that the level of pathogen contamination after this step would be under the tolerance levels set by safety guidelines.

The correlation between the reduction in pathogen levels and ozone exposure depicted in the study can be extrapolated to many different plant species. However, the study results are especially advantageous in showing that a non-toxic means for reducing harmful pathogen levels to acceptable safety standards in the Cannabis plant is available.

Cannabis is grown under many different conditions, both indoors and outdoors. As with all agricultural products, it is exposed to an extremely wide range of microorganisms.

The cannabinoids produced by the external glands of the Cannabis plant have well-documented antibacterial properties. Living Cannabis plants do not support high levels of bacterial growth, and pathogenic bacteria are unlikely to be associated with living Cannabis plants. There is also evidence for anti-fungal activity of certain cannabinoids, but fungal growth is not at all uncommon in Cannabis plants. Most of these mold and mildew species are plant pathogens, and not human ones; molds such as Botrytis cinerea may harm the Cannabis plant, but they are unlikely to harm humans.

Cannabis, as well as other plants such as herbs including mint and sage, citrus peel, some flowers and aromatic barks and woods, have distinct aromas produced by a terpenoid component in their essential oils. The distinct aromas that are given off by such plants are a product of which terpenoids predominate for that plant. For example, in the case of Cannabis, terpenoids and cannabinoids are secreted inside the Cannabis plant's glandular trichomes, and they have a parent compound in common (geranyl pyrophosphate). More than 200 terpenoids have been identified in Cannabis. The most common and most studied include limonene, myrcene, alpha-pinene, linalool, beta-caryophyllene, caryophllene oxide, nerolidol and phytol. Because many consumers prize the distinct smells produced by aromatic plants, it is important that the plants maintain those aromas even after being subjected to gaseous ozone treatment.

It has been determined that subjecting plants to concentrations of ozone between 1 ppm-1000 ppm for an amount of time in the range of 1 minute to 48 hours produces plant products that maintain the distinct smells produced by those plants and their corresponding terpenes, even after gaseous ozone treatment. Gaseous ozone treatment in these ranges provides significant reduction or elimination of pathogens, pesticides, and fungus, including yeast and mold, while maintaining the distinct smells intrinsic to aromatic plants. Further discussion regarding terpene content and gaseous ozone treatment is provided herein with respect to the discussion of FIGS. 15-18.

In an embodiment, the concentration of ozone to which the target is subjected is between about 1 ppm and about 1000 ppm, about 1 ppm and about 800 ppm, about 1 ppm and about 600 ppm, about 50 ppm and about 400 ppm, about 50 ppm and about 300 ppm, about 100 ppm and about 300 ppm, about 150 ppm and about 250 ppm, or about 180 ppm and about 220 ppm. In some embodiments, the concentration of ozone to which the target is subjected is greater than 20 ppm, greater than 50 ppm, greater than 75 ppm, greater than 100 ppm, greater than 125 ppm, greater than 150 ppm, greater than 175 ppm, greater than 200 ppm, greater than 225 ppm, greater than 250 ppm, greater than 275 ppm, greater than 300 ppm, greater than 400 ppm, greater than 500 ppm, or greater than 600 ppm. In some embodiments, the concentration of ozone to which the target is subjected is less than 700 ppm, less than 600 ppm, less than 500 ppm, less than 400 ppm, less than 350 ppm, less than 300 ppm, less than 275 ppm, less than 250 ppm, less than 225 ppm, less than 200 ppm, less than 175 ppm, less than 150 ppm, less than 125 ppm or less than 100 ppm. In a preferred embodiment, the concentration of ozone to which the target is subjected is between about 190 ppm to about 210 ppm.

Generally, it has been determined that the concentration of ozone used is related to the exposure time necessary to achieve a desired elimination of pathogens, pesticides, and fungus, including yeast and mold. For example, ozone levels as low as 1 ppm are effective at halting the growth process of mold or mildew if used over a longer period of time. As a further example, if a plant is subjected to a concentration of ozone of 200 ppm instead of 1 ppm, then less exposure time is necessary to achieve a desired elimination of pathogens, pesticides, and fungus, including yeast and mold.

Importantly, the concentration of ozone and amount of time a plant is exposed to the ozone must account for several factors when determining an effective concentration and exposure, including density of the plant (e.g., flower), the strain of the plant, and the surface area of plant that is exposed to ozone. For example, a denser strain of *cannabis* flower (e.g., Indica or Indica dominant strain) may require more exposure time to ozone than a less dense strain of flower (e.g., *Sativa* or *Sativa* dominant strain). In certain embodiments, if the strain of flower is too dense or too large (resulting in less surface area) then the plant may be modified (e.g., broken down into smaller pieces) to increase the surface area and obtain more effective treatment. If working with a *cannabis* plant, the exposures effect on cannabinoids (e.g., THC, CBGA, and THCA), terpene, trichomes, potency, flavor profile, and weight should be considered. For example, using a concentration of ozone (e.g., about 190 ppm to about 210 ppm) that effectively reduces or eliminates pathogens, pesticides, and fungus, including yeast and mold with little to no negative effects on the plants cannabinoids (e.g., THC, CBGA, and THCA), terpene, trichomes, potency, flavor profile, and weight is desirable.

In an embodiment, the time a plant is exposed to ozone is about 1 minute to about 48 hours, about 2 minutes to about 24 hours, about 3 minutes to about 18 hours, about 4 minutes to about 12 hours, about 5 minutes to about 6 hours, about 6 minutes to about 4 hours, about 7 minutes to about 2 hours, about 8 minutes to about 1.5 hours, about 10 minutes to about 1 hour, about 10 minutes to about 1 hour, about 12 minutes to about 50 minutes, about 14 minutes to about 30 minutes, about 16 minutes to about 25 minutes. In some embodiments, the time a plant is exposed to ozone is greater than 1 minute, greater than 5 minutes, greater than 10 minutes, greater than 15 minutes, greater than 20 minutes, greater than 30 minutes, greater than 45 minutes, greater than 1 hour, greater than 2 hours, greater than 6 hours, greater than 12 hours, greater than 24 hours or greater than 48 hours. In some embodiments, the time a plant is exposed to ozone is less than 48 hours, less than 24 hours, less than 12 hours, less than 10 hours, less than 8 hours, less than 6 hours, less than 4 hours, less than 3 hours, less than 2 hours, less than 1.5 hours, less than 1 hour, less than 50 minutes, less than 40 minutes, less than 30 minutes, less than 25 minutes, less than 20 minutes, less than 15 minutes, less than 10 minutes, less than 5 minutes, or less than 2 minutes. In a preferred embodiment, the time a plant is exposed to ozone is about 20 minutes to about 60 minutes.

In an embodiment, a plant is exposed to ozone at room temperature (e.g., 59° F. to 77° F.). In an embodiment, a plant is exposed to ozone at temperatures between 40° F. and 100° F. In certain embodiments, a plant is exposed to ozone at temperatures greater than about 50° F., greater than about 60° F., greater than about 70° F., greater than about 80° F., or greater than about 90° F. In certain embodiments, a plant is exposed to ozone at temperatures less than about 100° F., less than about 90° F., less than about 80° F., less than about 70° F., or less than about 60° F.

It has been determined in certain embodiments that exposing a *cannabis* flower to a concentration of ozone of 200 ppm for between about 20 minutes and 90 minutes can result in a reduction of 100,000 to 150,000 CFUs per hour without any change to the potency, flavor profile, terpenes or weight of the flower.

In an embodiment, exposure of a plant to ozone results in less than about 50,000 CFUs on the treated plant following ozone exposure, less than about 40,000 CFUs, less than about 30,000 CFUs, less than about 20,000 CFUs, less than about 10,000 CFUs, less than about 9,000 CFUs, less than about 8,000 CFUs, less than about 7,000 CFUs, less than about 6,000 CFUs, less than about 5,000 CFUs, less than about 4,000 CFUs, less than about 3,000 CFUs, less than about 2,000 CFUs, less than about 1,000 CFUs, less than about 500 CFUs, or no measurable CFUs.

Any danger to humans from consumption of pathogens associated with the *Cannabis* plant would be due to a combination of factors across one or more of the stages of: growth, processing, and use. Pathogens would have to arrive on the plant during growing or processing, survive all processing and use steps, and then they—or their toxins— would have to be transferred to a human host in a way that allows them to cause disease.

Although *Cannabis*, unlike many other plants, has inherent antibacterial properties, is dried well and is usually then heated during processing or use, microbial threats still exist. For example, detection of significant levels of *E. Coli* are strong evidence of problems during growing or processing, including contaminated soil or water, or improper handling.

*E. Coli* is accepted to be the optimal indicator organism for the identification of possible fecal contamination. Were pathogenic bacteria such as *E. Coli* or *Salmonella* to be present, they would likely have arrived through this type of pathway, therefore samples for *E. Coli* are both higher risk and indicative of general production problems that need to be addressed.

Turning back to FIG. 1, test results for the study described above are provided. The X-axis of graph 100 is divided into average test results for gaseous ozone treatment of *Cannabis* inoculated with *E. Coli, Salmonella, Listeria* and *Candida* compared against control (i.e., inoculated *Cannabis* not treated with ozone). The Y-axis of graph 100 depicts averages for the test results, in log values of colony-forming units per gram (CFU/gram), for the study. Log values for average CFU/gram for *E. Coli* are shown at 102. Log values for average CFU/gram for *Salmonella* are shown at 104. Log values for average CFU/gram for *Listeria* are shown at 106 and log values for average CFU/gram for *Candida* are shown at 108.

Figure 2:
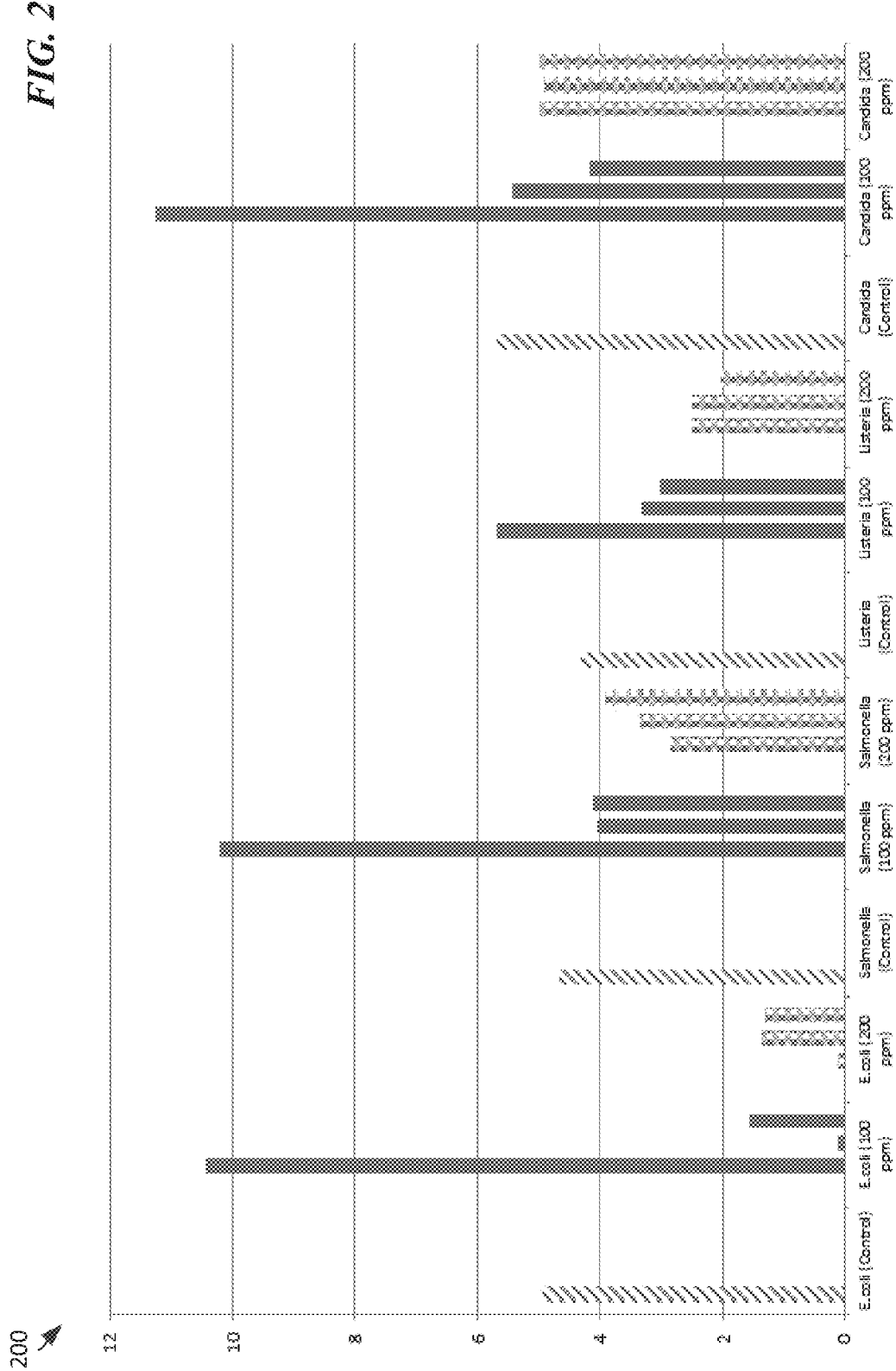
FIG. 2 is a graph showing microbial counts for individual trials after treatment of plant pathogens with gaseous ozone.

Moving to FIG. 2, test results for the study described above are depicted in graph 200. Microbial counts for the individual trials conducted during that study are shown for *E. Coli, Salmonella, Listeria* and *Candida* against control.

Figure 3:
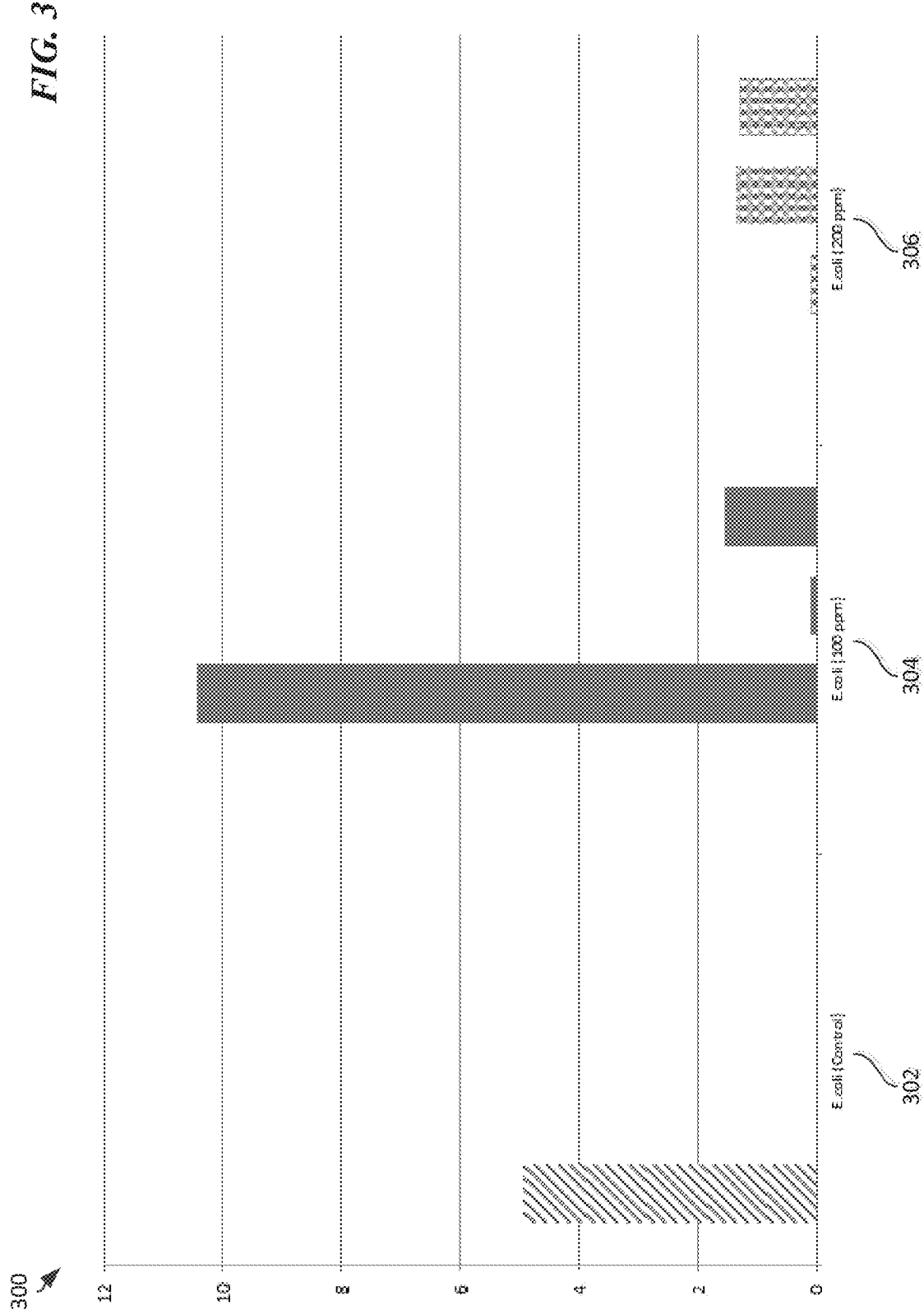
FIG. 3 is a graph showing *E. Coli* counts after treatment with gaseous ozone at 100 ppm and 200 ppm compared with a control group.

FIG. 3 is a graph 300 showing *E. Coli* counts after treatment with gaseous ozone compared with a control group. Results for the control group are shown at 302, results for the group treated at an ozone concentration of 100 ppm are shown at 304 and results for the group treated at an ozone concentration of 200 ppm are shown at 306.

Figure 4:
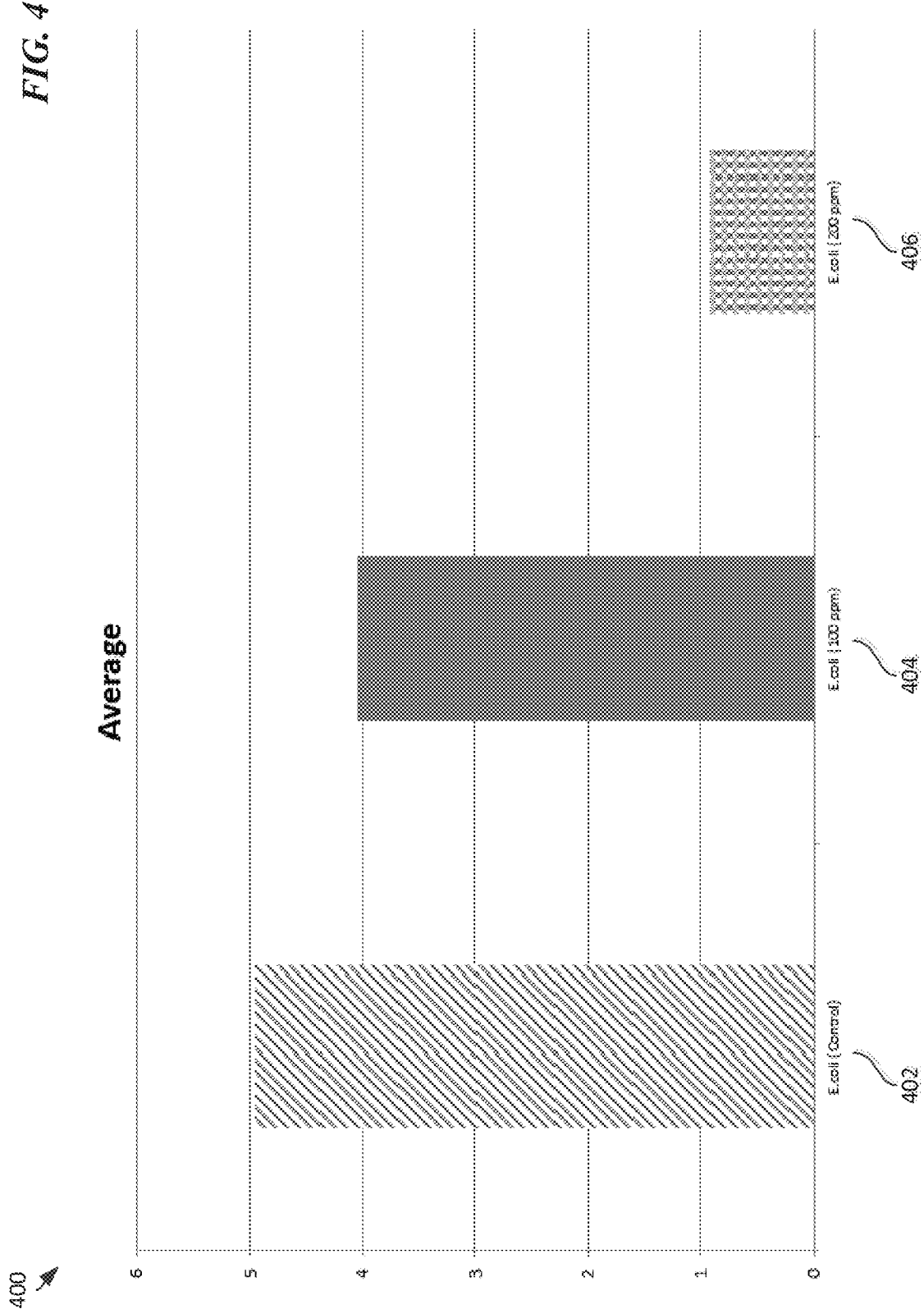
FIG. 4 is a graph showing the average *E. Coli* counts from multiple trials after treatment with gaseous ozone at 100 ppm and 200 ppm compared with a control group.

Turning to FIG. 4 average *E. Coli* counts after treatment with gaseous ozone compared with a control group are depicted in graph 400. Results for the control group are shown at 402, average results for the group treated at an ozone concentration of 100 ppm are shown at 404 and average results for the group treated at an ozone concentration of 200 ppm are shown at 406.

Figure 5:
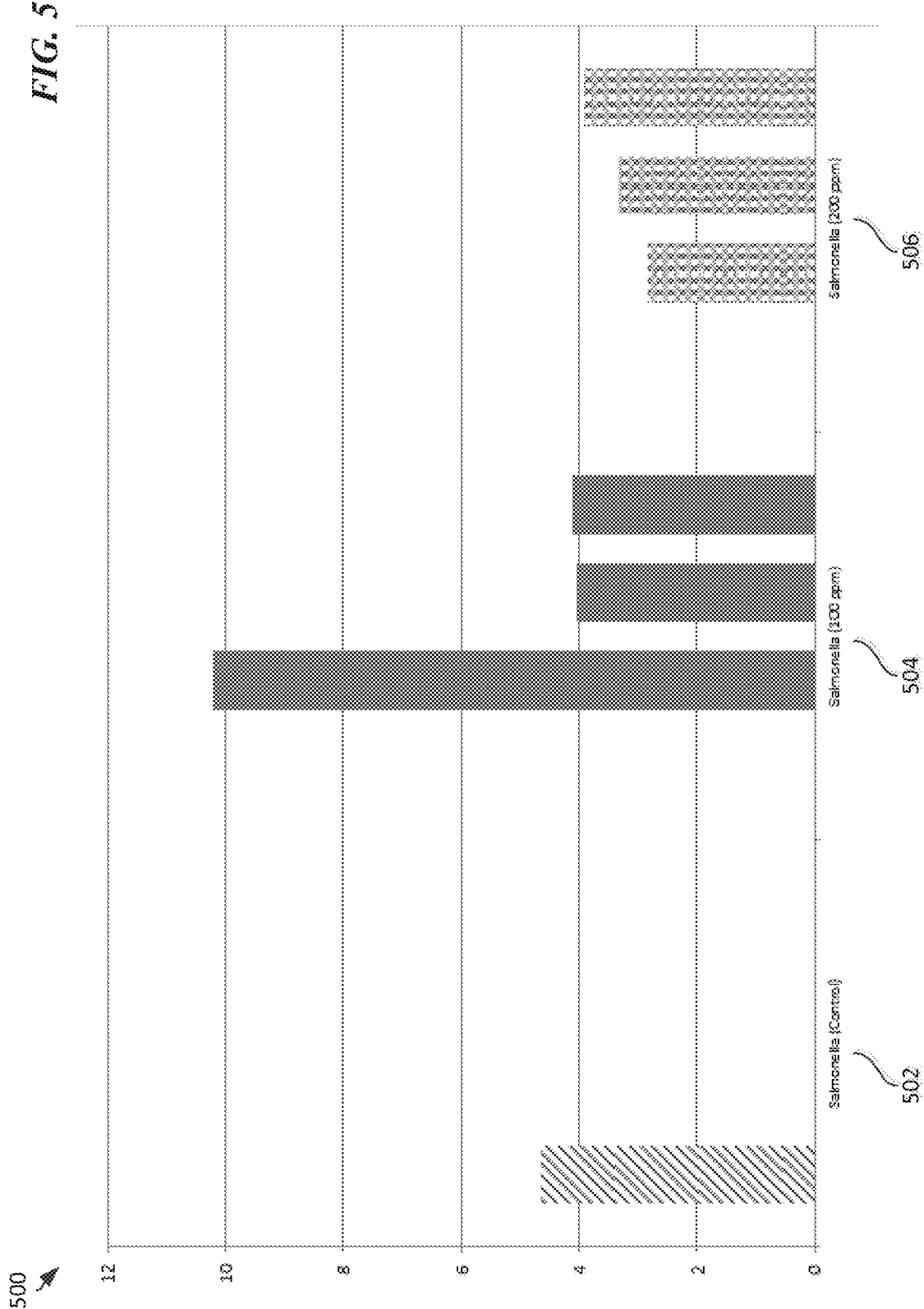
FIG. 5 is a graph showing *Salmonella* counts after treatment with gaseous ozone at 100 ppm and 200 ppm compared with a control group.

FIG. 5 is a graph 500 showing *Salmonella* counts after treatment with gaseous ozone compared with a control group. Results for the control group are shown at 502, results for the group treated at an ozone concentration of 100 ppm are shown at 504 and results for the group treated at an ozone concentration of 200 ppm are shown at 506.

Figure 6:
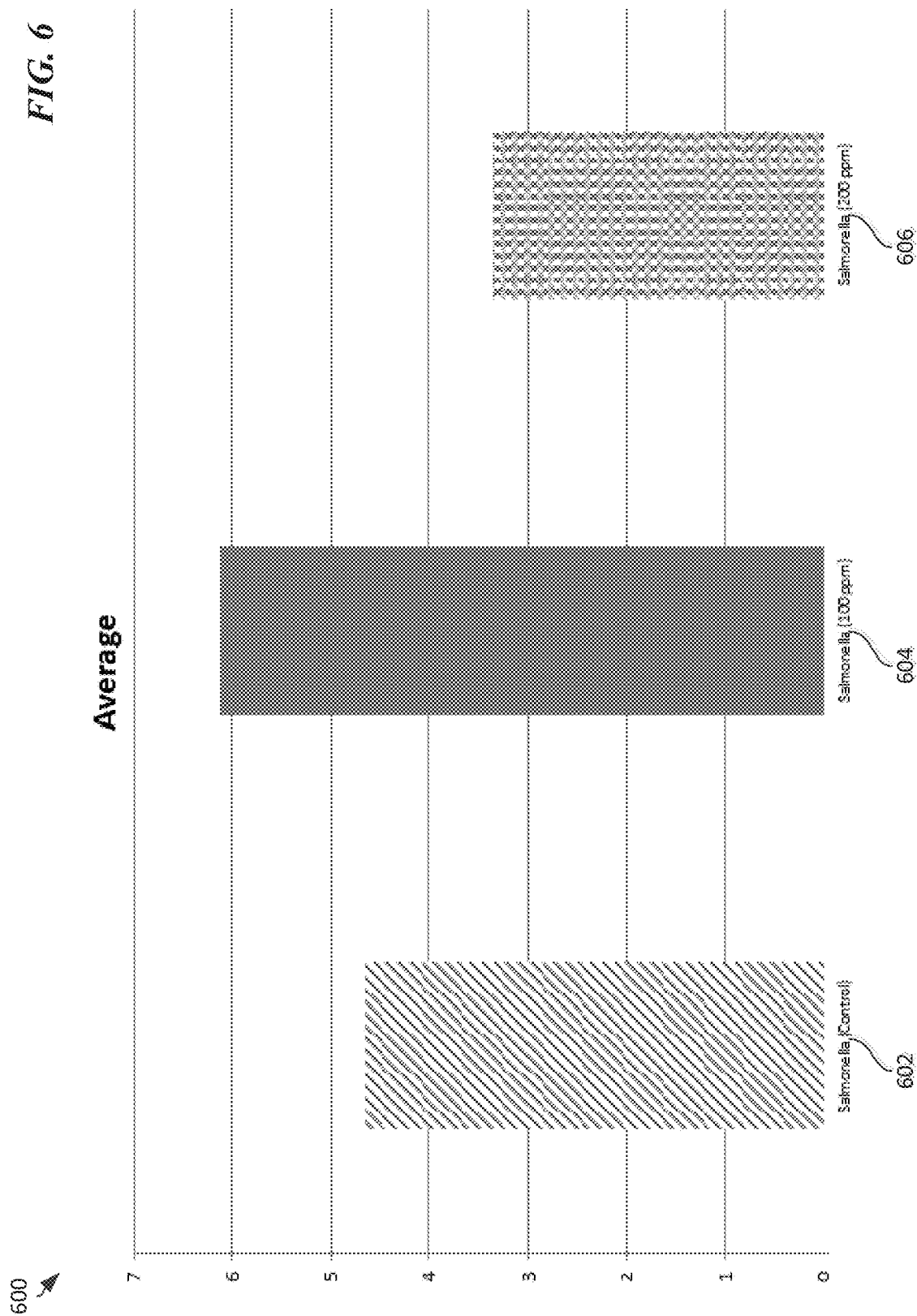
FIG. 6 is a graph showing the average *Salmonella* counts from multiple trials after treatment with gaseous ozone at 100 ppm and 200 ppm compared with a control group.

FIG. 6 shows a graph 600 depicting average *Salmonella* counts after treatment with gaseous ozone compared with a control group. Results for the control group are shown at 602, average results for the group treated at an ozone concentration of 100 ppm are shown at 604 and average results for the group treated at an ozone concentration of 200 ppm are shown at 606.

Figure 7:
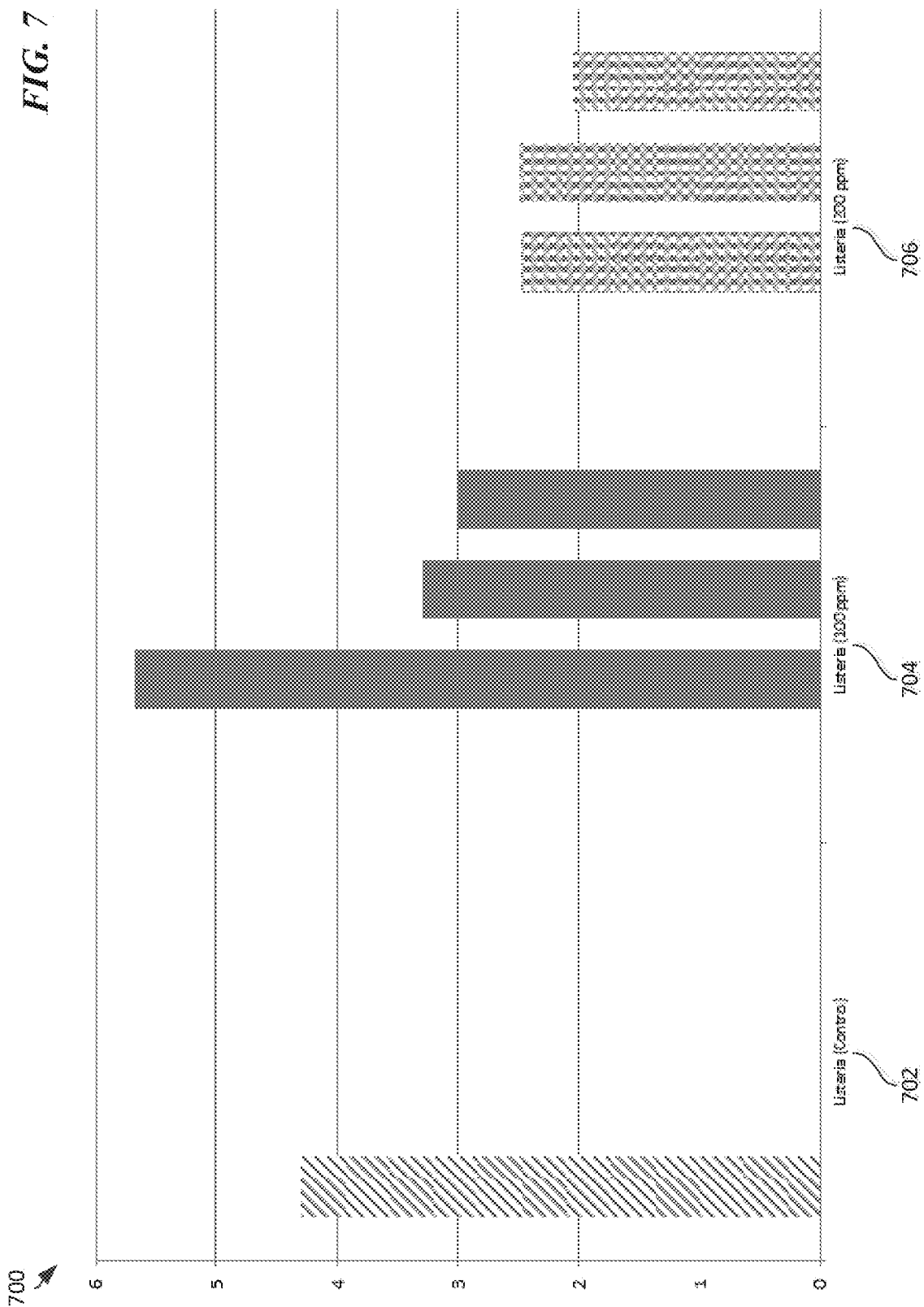
FIG. 7 is a graph showing *Listeria* counts after treatment with gaseous ozone at 100 ppm and 200 ppm compared with a control group.

FIG. 7 is a graph 700 showing *Listeria* counts after treatment with gaseous ozone compared with a control group. Results for the control group are shown at 702, results for the group treated at an ozone concentration of 100 ppm are shown at 704 and results for the group treated at an ozone concentration of 200 ppm are shown at 706.

Figure 8:
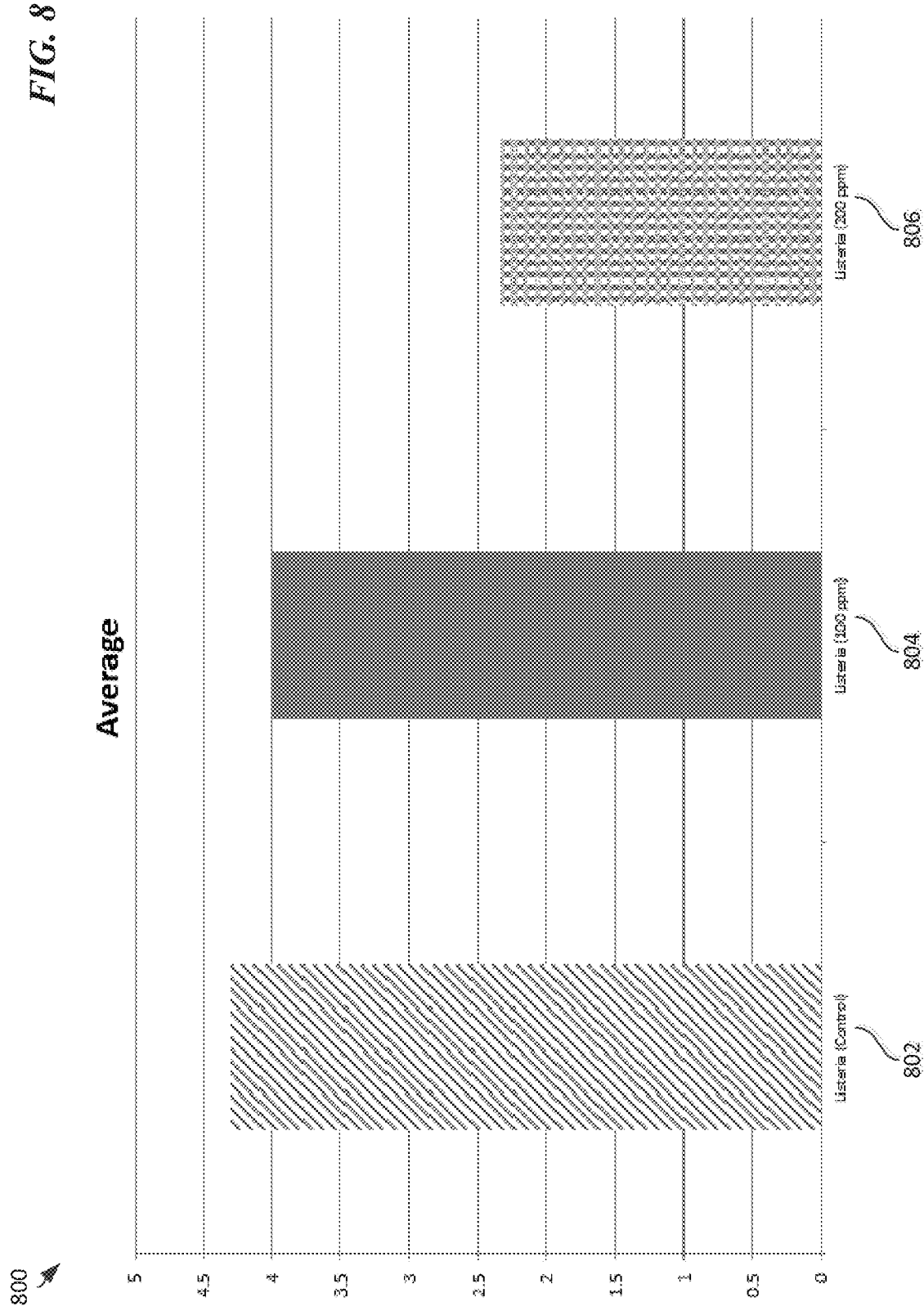
FIG. 8 is a graph showing the average *Listeria* counts from multiple trials after treatment with gaseous ozone at 100 ppm and 200 ppm compared with a control group.

FIG. 8 shows a graph 800 depicting average *Listeria* counts after treatment with gaseous ozone compared with a control group. Results for the control group are shown at 802, average results for the group treated at an ozone concentration of 100 ppm are shown at 804 and average results for the group treated at an ozone concentration of 200 ppm are shown at 806.

Figure 9:
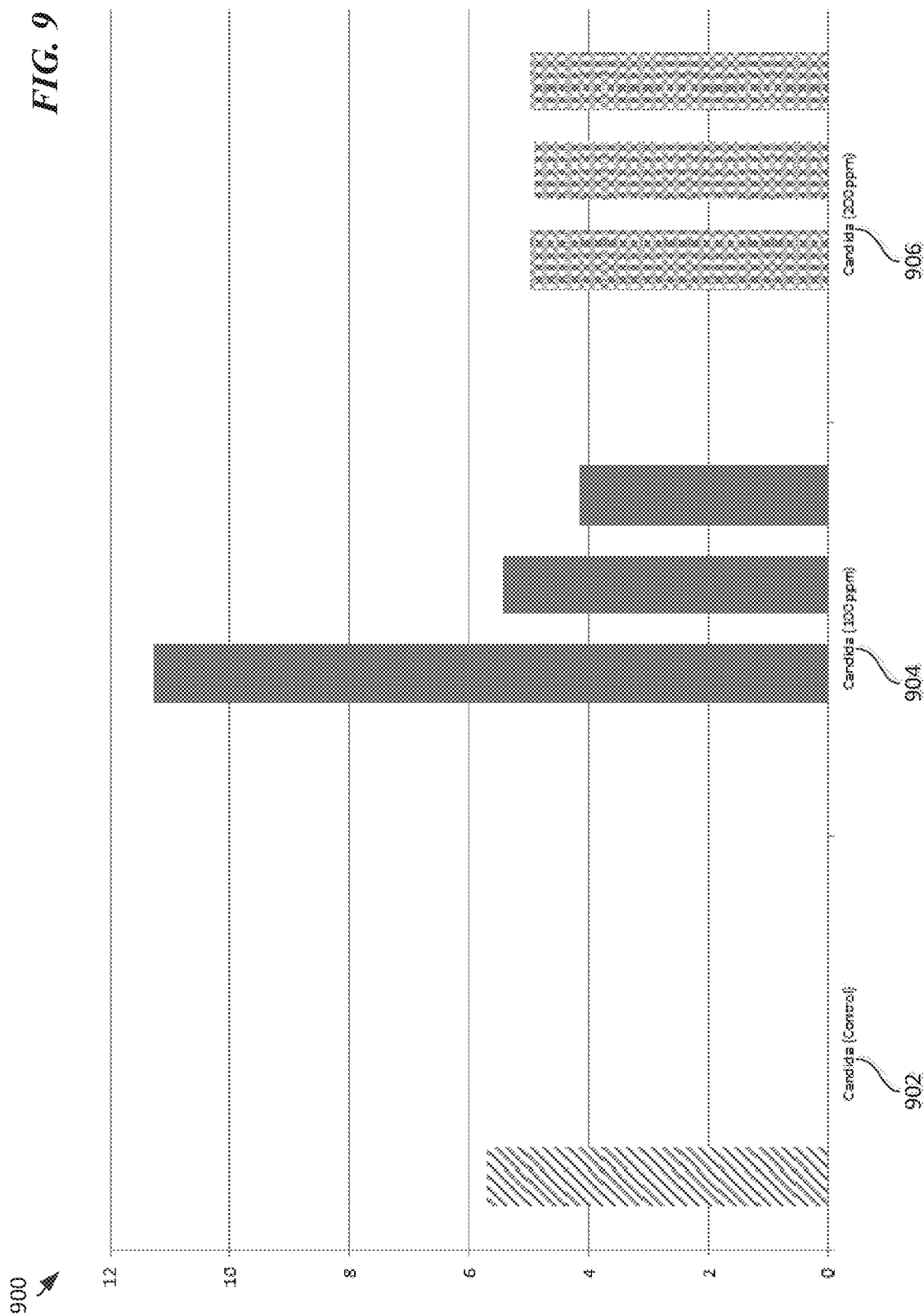
FIG. 9 is a graph showing *Candida* counts after treatment with gaseous ozone at 100 ppm and 200 ppm compared with a control group.

FIG. 9 is a graph 900 showing *Candida* counts after treatment with gaseous ozone compared with a control group. Results for the control group are shown at 902, results for the group treated at an ozone concentration of 100 ppm are shown at 904 and results for the group treated at an ozone concentration of 200 ppm are shown at 906.

Figure 10:
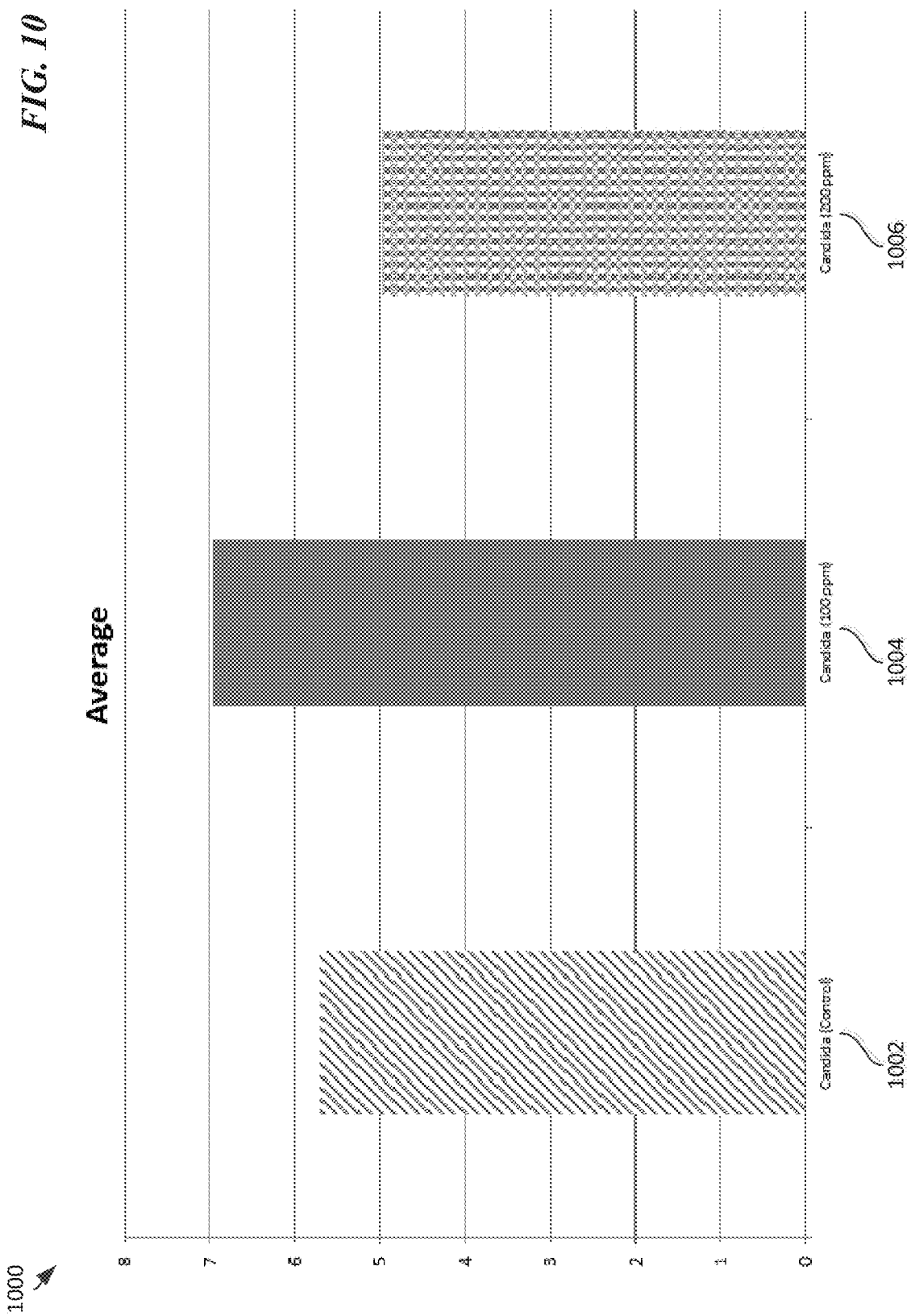
FIG. 10 is a graph showing the average *Candida* counts from multiple trials after treatment with gaseous ozone at 100 ppm and 200 ppm compared with a control group.

FIG. 10 shows a graph 1000 depicting average *Candida* counts after treatment with gaseous ozone compared with a control group. Results for the control group are shown at 1002, average results for the group treated at an ozone concentration of 100 ppm are shown at 1004 and average results for the group treated at an ozone concentration of 200 are shown at 1006.

Figure 11:
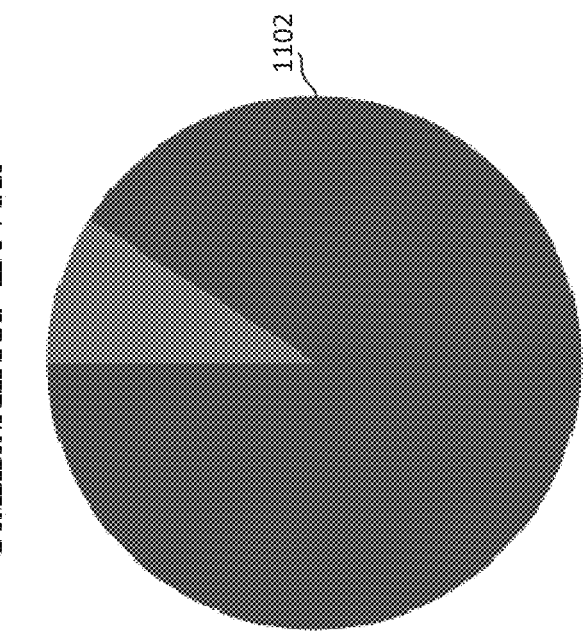
FIG. 11 is a graph and corresponding chart showing cannabinoid levels for a first strain of *cannabis* not treated with gaseous ozone.
Figure 12:
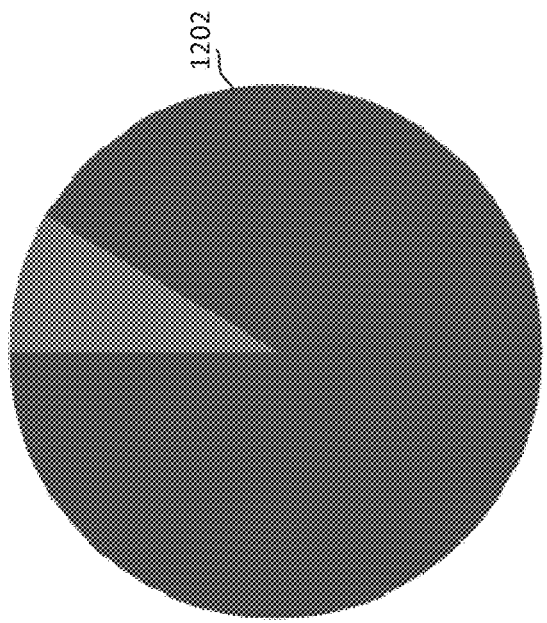
FIG. 12 is a graph and corresponding chart showing cannabinoid levels for a cannabinoid test run on a first strain of *cannabis* after treatment with gaseous ozone.

FIG. 11 and FIG. 12 depict graphs 1102 and 1202 showing cannabinoid levels for a first strain of *cannabis*. The results shown in relation to FIG. 11 are for a control sample (i.e., a *cannabis* sample that has not been subjected to gaseous ozone). The results shown in relation to FIG. 12 are for a sample that was treated with gaseous ozone according to the methods described herein. Also shown are detailed charts 1104 and 1204 depicting more precise percentages of the cannabinoid levels for that tested strain, including levels for THC-A, CBD, CBD-A, CBN, CBG, CBG-A, CBC and CHCV. THC-A and CBD-A are the "inactive" acidic forms of the THC and CBD molecules, which convert THC and CBD given time and/or heat. THC-A and CBD-A counts, as reflected in the graphs 1102 and 1202 and the charts 1104 and 1204 have been adjusted to account for the greater weight of the acidic molecules.

Figure 13:
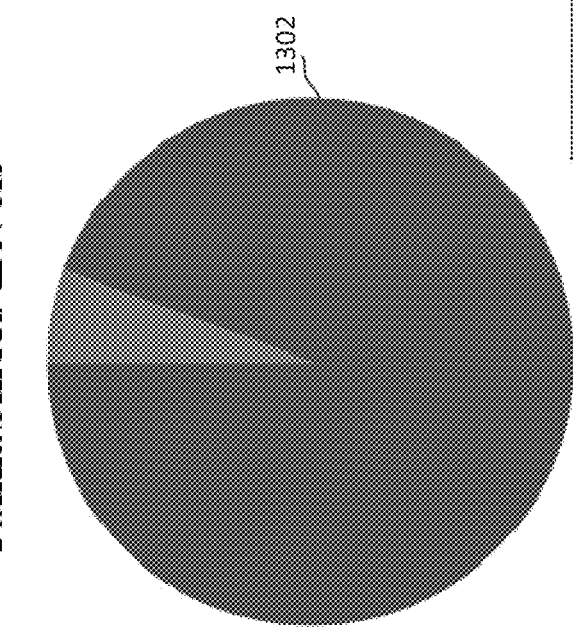
FIG. 13 is a graph and corresponding chart showing cannabinoid levels for a second strain of *cannabis* not treated with gaseous ozone.
Figure 14:
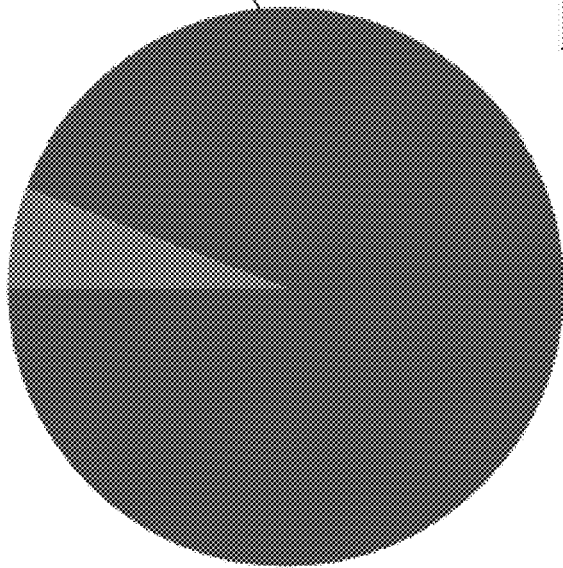
FIG. 14 is a graph and corresponding chart showing cannabinoid levels for a cannabinoid test run on a second strain of *cannabis* after treatment with gaseous ozone.

FIG. 13 and FIG. 14 depict graphs 1302 and 1402 showing cannabinoid levels for a second strain of *cannabis*. The results in relation to FIG. 13 are for a control sample (i.e., a *cannabis* sample that has not been subjected to gaseous ozone). The results shown in relation to FIG. 14 are for a sample that was treated with gaseous ozone according to the methods described herein. Also shown are detailed charts 1304 and 1404 showing more precise percentages of the cannabinoid levels for that second tested strain, including levels for THC-A, CBD, CBD-A, CBN, CBG, CBG-A, CBC and CHCV. THC-A and CBD-A counts, as reflected in the graphs 1302 and 1402 and the charts 1304 and 1404 have been adjusted to account for the greater weight of the acidic molecules.

The results from the tests as shown in FIGS. 11-14 show that cannabinoid levels are not adversely affected by treatment with gaseous ozone according to methods described herein. Rather, total THC for the tested samples for both the control samples and samples treated with gaseous ozone according to the methods described herein were significantly similar. That is, *cannabis* samples treated with gaseous ozone maintain cannabinoid concentrations similar to *cannabis* samples that have not been treated with gaseous ozone.

Figure 15:
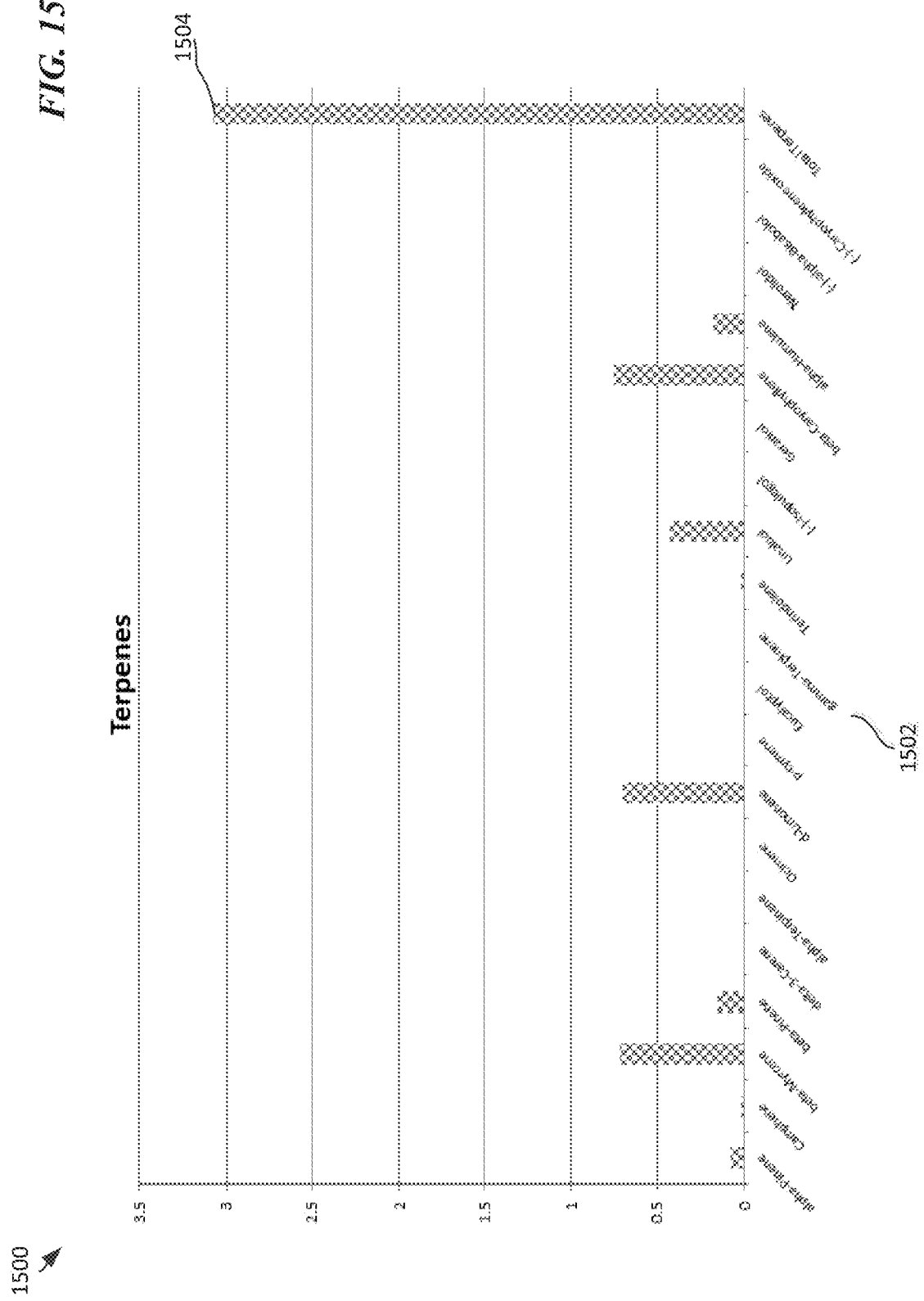
FIG. 15 is a graph showing terpene levels for a first strain of *cannabis* not treated with gaseous ozone.
Figure 16:
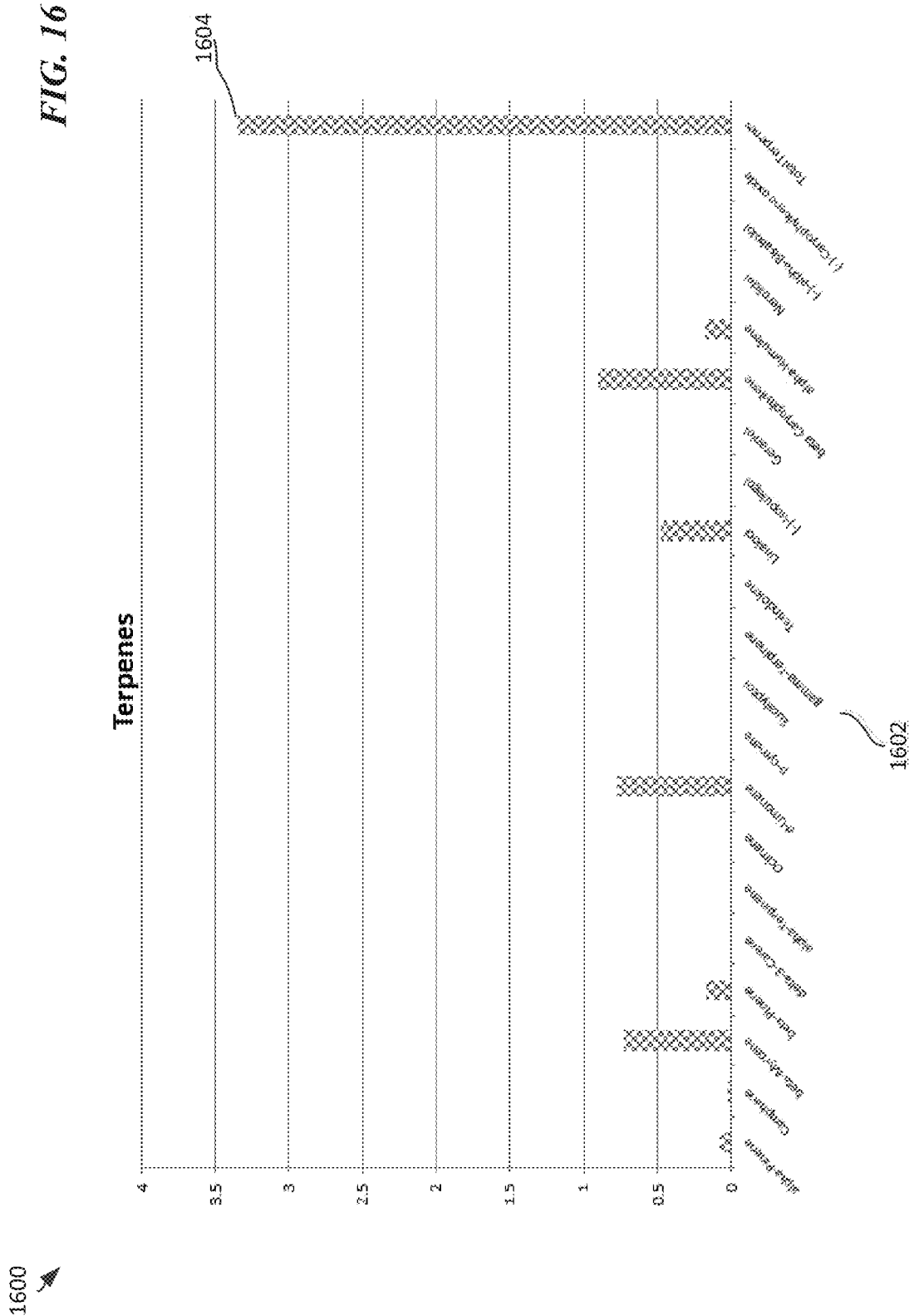
FIG. 16 is a graph showing terpene levels for a terpene test run on a first strain of *cannabis* after treatment with gaseous ozone.

FIG. 15 and FIG. 16 are graphs 1500 and 1600 depicting various levels of terpenes 1502 and 1602 found in a first strain of *cannabis*. The Y axis of the graphs 1500 and 1600 represent terpene concentration percent by weight. The results shown in relation to FIG. 15 are for a control sample (i.e., a *cannabis* sample that has not been subjected to gaseous ozone). The results shown in relation to FIG. 16 are for a sample that was treated with gaseous ozone according to the methods described herein. Also shown in the graphs 1500 and 1600 is the total amount of terpenes 1504 and 1604 found in the first strain for both the control samples (FIG. 15) and the treated samples (FIG. 16).

Figure 17:
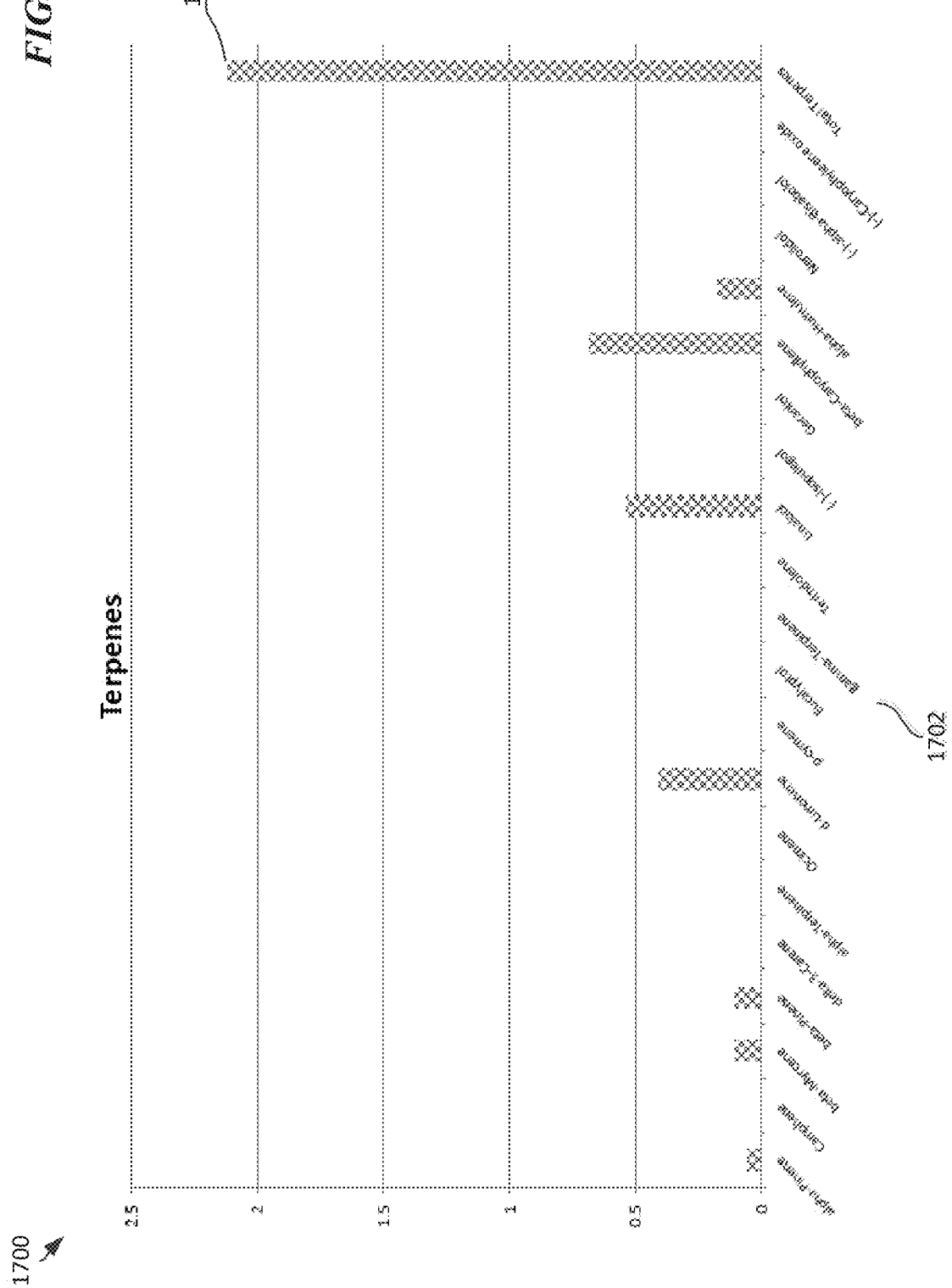
FIG. 17 is a graph showing terpene levels for a second strain of *cannabis* not treated with gaseous ozone.
Figure 18:
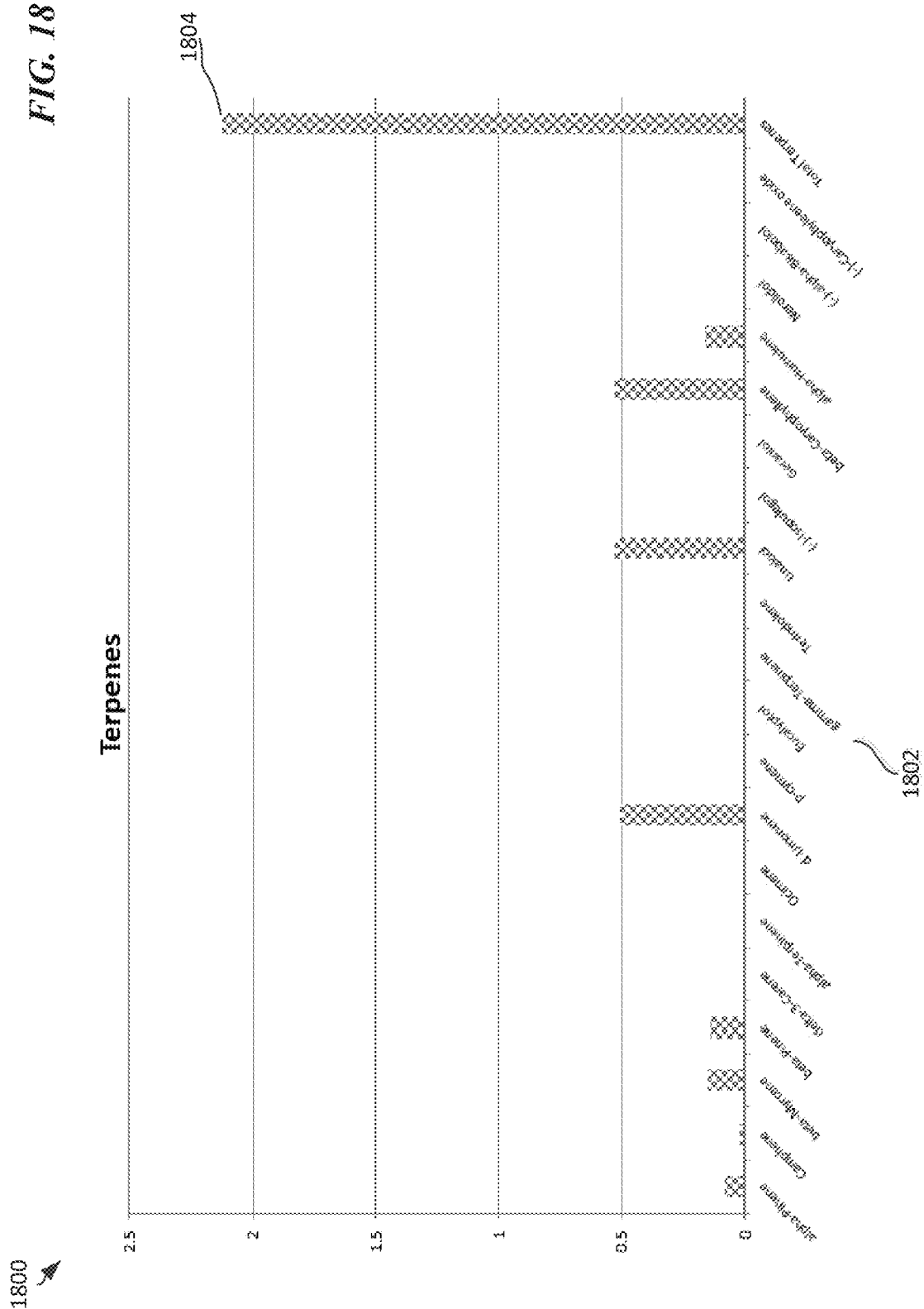
FIG. 18 is a graph showing terpene levels for a test run on a second strain of *cannabis* after treatment with gaseous ozone.

FIG. 17 and FIG. 18 are graphs 1700 and 1800 depicting various levels of terpenes 1702 and 1802 found in a second strain of *cannabis*. The Y axis of the graphs 1700 and 1800 represent terpene concentration percent by weight. The results shown in relation to FIG. 17 are for a control sample (i.e., a *cannabis* sample that has not been subjected to gaseous ozone). The results shown in relation to FIG. 18 are for a sample that was treated with gaseous ozone according to the methods described herein. Also shown in graphs 1700 and 1800 is the total amount of terpenes 1704 and 1708 found in the second strain for both control samples (FIG. 17) and treated samples (FIG. 18).

The results of the tests as shown in FIGS. 15-18 show that terpene levels are not adversely affected by treatment with gaseous ozone according to methods described herein. Rather, total terpene levels for the tested samples for both the control samples and samples treated with gaseous ozone were significantly similar. That is, *cannabis* samples treated with gaseous ozone maintain terpene concentrations similar to *cannabis* samples that have not been treated with gaseous ozone.

Terpene Testing Methods: A testing methodology known as Headspace Gas-Chromatography with Flame Ionization Detection, or headspace GC-FID was used. This method is widely used in the environmental and pharmaceutical industries to analyze for product or environmental contamination. For each test, a small sample of *cannabis* is used. The sample is heated in an airtight vial to vaporize the residual solvents, sample the headspace in the vial and inject the headspace sample into a gas chromatograph for chemical analysis. In analyzing sample headspace, various matrix interferences were screened from the concentrate. The terpene content for the samples may represent lower than expected results as no correction for moisture content was performed. As such, some terpenes may have evaporated upon drying giving lower than expected terpene results.

Figure 19:
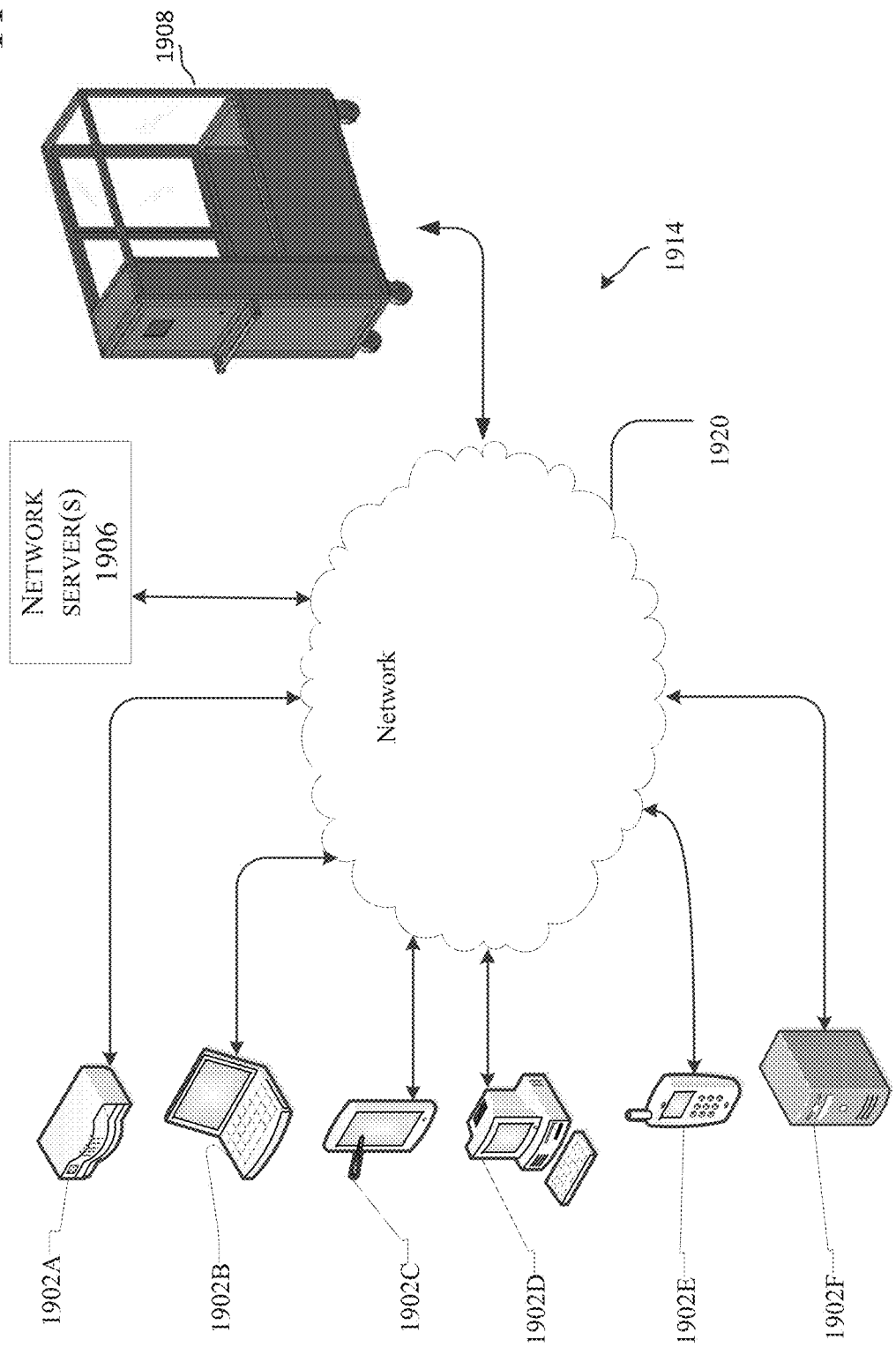
FIG. 19 is a simplified diagram of a distributed computing system in which aspects of the present invention may be practiced.

FIG. 19 is a simplified diagram of a distributed computing system 1914 in which aspects of the present invention may be practiced. According to examples, any of computing devices 1902A (a modem), 1902B (a laptop computer), 1902C (a tablet), 1902D (a personal computer), 1902E (a smart phone), and 1902F (a server) may be used to send, receive and evaluate signals from pathogen reduction device 1908 via one or more network servers 1906 and a network 1920. Such signals may include data related to ozone concentration, temperature and time of exposure, for example.

According to some aspects pathogen reduction device 1908 may be a stationary or fixed device. According to other aspects pathogen reduction device 1908 may be a mobile device. For example, pathogen reduction device 1908 may stand on a plurality of wheels for moving the device from one place to another. The wheels may be fixed to the device or they may be readily removed and put back on, by for example, a pop out mechanism. According to an embodiment pathogen reduction device 1908 may have the following dimensions: a length of 4 feet, 4 inches; a width of 2 feet, 0 inches; and a height of 5 feet, 2 inches. With wheels attached the height of the pathogen reduction device may be 5 feet, 5 inches.

According to additional examples pathogen reduction device 1908 may contain a plurality of racks within an ozone chamber. The racks may be positioned suitably for treating plants on each rack level in the pathogen reduction device 1908. For example, the racks may be positioned at 6 inch vertical intervals within the pathogen reduction device 1908. The racks may be made of metal sliders and a metal mesh shelf to effectively ozonate a plant. They may also include a lip around the shelf to prevent loss of a treated plant. For example, the shelves may include a 3 inch lip such that treated plant product is not lost. In accordance with these examples it should be appreciated that such a racking system allows for the processing (i.e., gaseous ozone treatment) of approximately 33-44 pounds of plant product every 20 minutes.

Pathogen reduction device 1908 may comprise one or more of a controller, an ozone system (including an ozone generator and an ozone chamber) and an oxygen concentrator.

Pathogen reduction device 1908 according to certain embodiments may include safety mechanisms including but not limited to a destructor for venting gaseous ozone, providing a mechanism for immediately degrading ozone back to $O_2$, a leak sensor in communicative contact with an alarm display and a safety interlock. According to aspects, one or more of these safety mechanisms may be employed as part of pathogen reduction device 1908 as well as distributed computing system 1914.

A controller as described herein in association with the pathogen reduction device 1908 may control and operate each component within the pathogen reduction device 1908 including the ozone chamber. The controller may comprise one or more processors and a memory coupled to the one or more processors. The memory may store instructions that when executed by the one or more processors cause the one or more processors to implement one or more steps, including: determining a concentration of gaseous ozone in an ozone chamber; adjusting the concentration of gaseous ozone in the ozone chamber; adjusting the ambient temperature in the ozone chamber; continuously monitoring the concentration of gaseous ozone and the ambient temperature in the ozone chamber and automatically adjusting the monitored concentration and temperature to a preset concentration and preset temperature.

The controller may also include a graphical user interface for touch screen operation and system interaction. Integrated sensors may be configured to monitor conditions in the pathogen reduction device 1908 so that proper action can be taken to reduce pathogen levels associated with plants being treated in the pathogen reduction device 1908. For example, integrated sensors may provide, via a graphical user interface on the pathogen reduction device or a graphical user interface on computing devices 1902A-F, an indication that an ozone leak has occurred. The controller may be further configured to shut down one or more of the elements described in the pathogen reduction methods and systems described herein to protect the various components of the pathogen reduction device 1908. The controller may also be configured to send a signal to one or more of computing devices 1902A-F if a sensor has failed such that remedial action can be taken.

Figure 20:
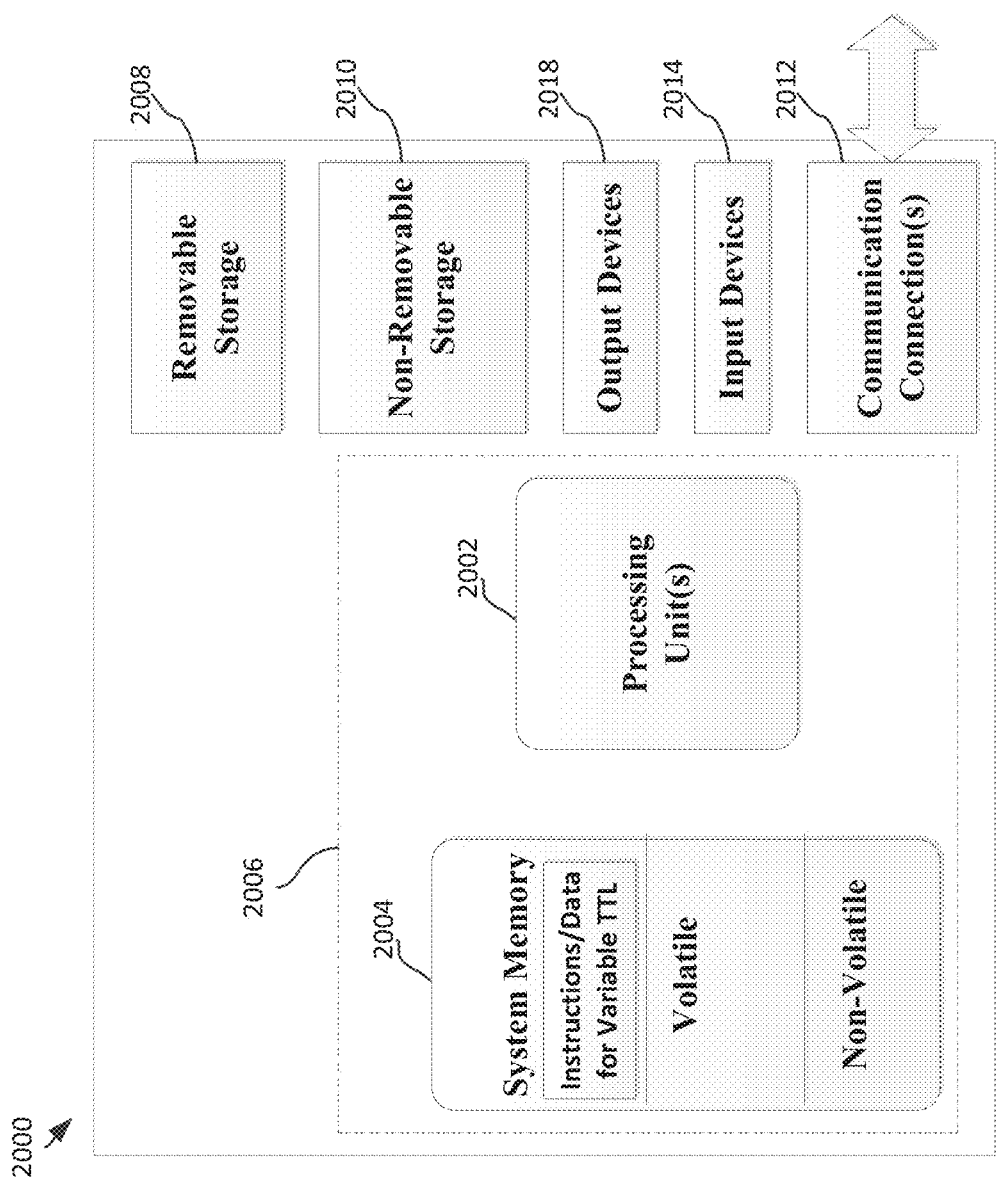
FIG. 20 illustrates one example of a suitable operating environment 1200 in which aspects of the present invention may be implemented.
Figure 21A:
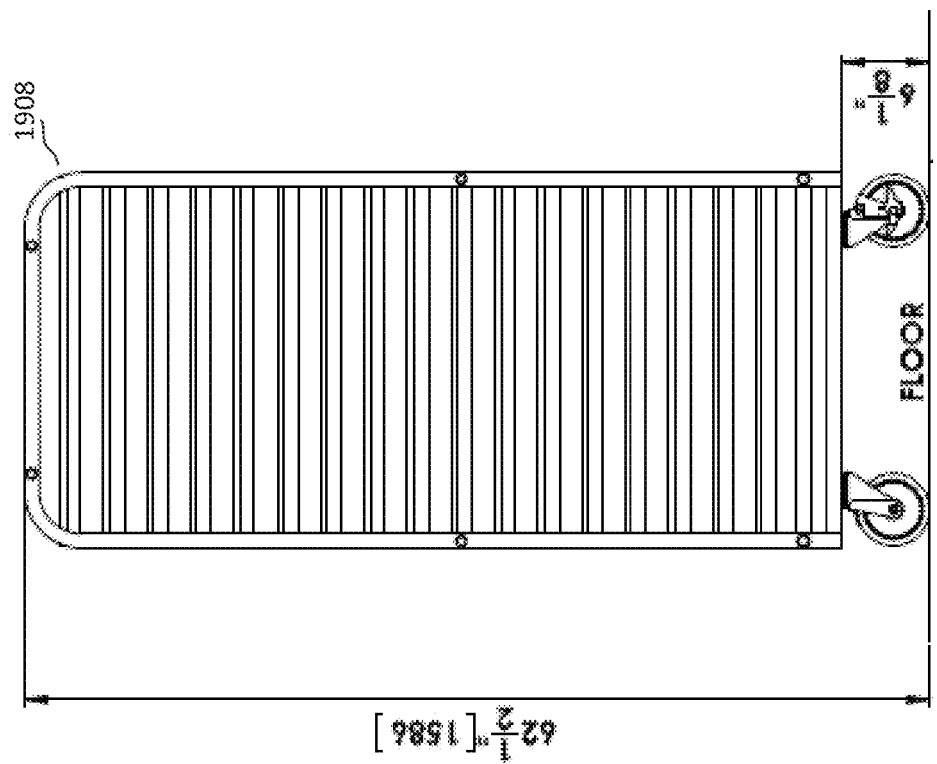
FIG. 21A illustrates a side profile of an embodiment of the pathogen reduction device 1908.
Figure 21B:
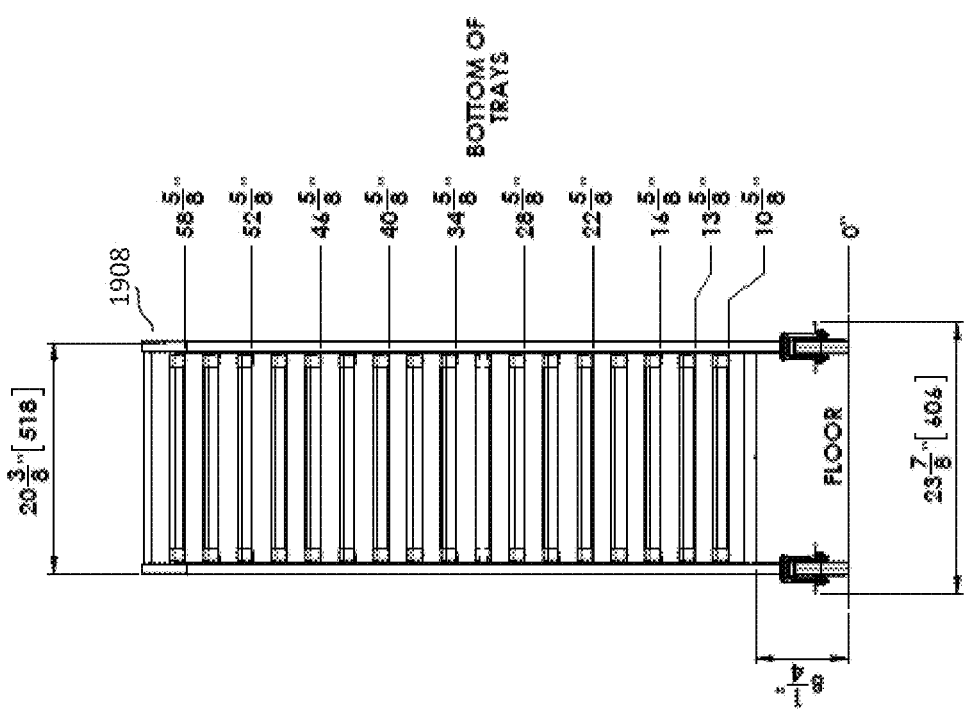
FIG. 21B illustrates a back profile of an embodiment of the pathogen reduction device 1908.
Figure 21D:
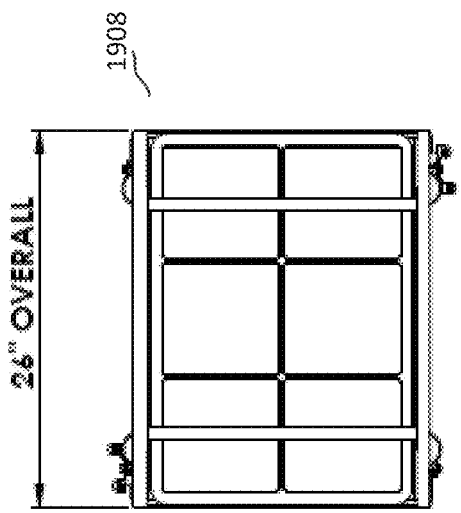
FIG. 21D illustrates a top profile of an embodiment of the pathogen reduction device 1908.
Figure 22:
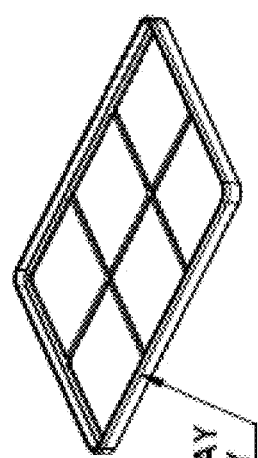
FIG. 22 illustrates an embodiment of a tray used within the pathogen reduction device 1908 to hold plant while it is exposed to ozone.

FIG. 20 illustrates one example of a suitable operating environment 2000 in which one or more of the present embodiments may be implemented. FIG. 20 provides only one example of a suitable operating environment and is not intended to suggest any limitation as to the scope of use or functionality. Other well-known computing systems, environments, and/or configurations that may be suitable for use include, but are not limited to, personal computers, server computers, hand-held or laptop devices, multiprocessor systems, microprocessor-based systems, programmable consumer electronics such as smart phones, network PCs, minicomputers, mainframe computers, distributed computing environments that include any of the above systems or devices, and the like.

In its most basic configuration, operating environment 2000 typically includes at least one processing unit 2002 and memory 2004. Depending on the exact configuration and type of computing device, memory 2004 (storing, among other things, reputation information, category information, cached entries, instructions to perform the methods disclosed herein, etc.) may be volatile (such as RAM), nonvolatile (such as ROM, flash memory, etc.), or some combination of the two. This most basic configuration is illustrated in FIG. 20 by dashed line 2006. Further, environment 2000 may also include storage devices (removable, 2008, and/or non-removable, 2010) including, but not limited to, magnetic or optical disks or tape. Similarly, environment 2000 may also have input device(s) 2014 such as keyboard, mouse, pen, voice input, etc. and/or output device(s) 2016 such as a display, speakers, printer, etc. Also included in the environment may be one or more communication connections, 2012, such as LAN, WAN, point to point, etc.

Operating environment 2000 typically includes at least some form of computer readable media. Computer readable media can be any available media that can be accessed by processing unit 2002 or other devices comprising the operating environment.

By way of example, and not limitation, computer readable media may comprise computer storage media and communication media. Computer storage media includes volatile and nonvolatile, removable and non-removable media implemented in any method or technology for storage of information such as computer readable instructions, data structures, program modules or other data. Computer storage media includes, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other tangible medium which can be used to store the desired information. Computer storage media does not include communication media.

Communication media embodies computer readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer readable media.

The operating environment 2000 may be a single computer operating in a networked environment using logical connections to one or more remote computers. The remote computer may be a personal computer, a server, a router, a network PC, a peer device or other common network node, and typically includes many or all of the elements described above as well as others not so mentioned. The logical connections may include any method supported by available communications media. Such networking environments are commonplace in offices, enterprise-wide computer networks, intranets and the Internet.

Aspects described herein may be employed using software, hardware, or a combination of software and hardware to implement and perform the systems and methods disclosed herein. Although specific devices have been recited throughout the disclosure as performing specific functions, one of skill in the art will appreciate that these devices are provided for illustrative purposes, and other devices may be employed to perform the functionality disclosed herein without departing from the scope of the disclosure.

It has been determined that an embodiment of a disclosed pathogen reduction device can ensure a constant level of ozone gas (e.g., 200 ppm) throughout the exposure time. In addition, an embodiment of a disclosed pathogen reduction device is capable of treating a small sample (e.g., less than 10 grams of flower) or large sample (e.g., enough sample to completely fill all the racks of the pathogen reduction device, which varies depending on device size but can be large, e.g., 50 lbs) without negatively affecting the effectiveness of the ozone treatment.

The ability of ozone to reduce pesticide residue using an embodiment of a disclosed pathogen reduction device was evaluated. In this series of experiments, Myclobutanil and Bifenizate were purchased in liquid formulations (Myclobutanil at 19.7% from Dow AgroSciences as Eagle® 20EW and Bifenazate at 22.6% from Chemtura Corporation as Floramite® SC). The pesticides were sprayed on homogenized hemp flower and air dried. Dried hemp flower with pesticide was then exposed to treatment with 200 ppm of ozone for 20 minutes. Non pesticide treated hemp, pesticide treated hemp, and pesticide treated hemp that was exposed to ozone were analyzed by spectrometry using AOAC official method 2007.01. The results are disclosed below in Table 3 were Matrix Blank is non pesticide treated hemp (negative control), Control is pesticide treated hemp that was not exposed to ozone, and Sample 1, Sample 2, and Sample 3 are three samples of pesticide treated hemp that was exposed to ozone at 200 ppm for 20 minutes.

Ozone treatment of hemp contaminated with Myclobutanil or Bifenizate was effective. For example, exposing hemp contaminated with Myclobutanil for 20 minutes at 200 ppm ozone resulted in an average reduction of 0.18 ppm Myclobutanil across the three samples tested. Similarly, exposing hemp contaminated with Bifenizate for 20 minutes at 200 ppm ozone resulted in an average reduction of 0.1 ppm Bifenizate across the three samples tested.

TABLE 3

This table discloses the ability of ozone treatment to effectively reduce Myclobutanil or Bifenizate.

| Compound | Matrix Blank (mg/kg) | Control (mg/kg) | Sample 1 (mg/kg) | Sample 2 (mg/kg) | Sample 3 (mg/kg) |
|---|---|---|---|---|---|
| Myclobutanil | LOD | 0.5 | 0.39 | 0.28 | 0.28 |
| Bifenazate | LOD | 0.34 | 0.28 | 0.21 | 0.22 |

"LOD" stands for below the limit of detection.

The ability of ozone to reduce fungus using an embodiment of a disclosed pathogen reduction device was also evaluated. In this series of experiments, homogenized *cannabis* flower with a total yeast and mold bio-burden exceeding 10,000 CFU/g was exposed to ozone using an embodiment of a disclosed pathogen reduction device. 20 gram samples of the *cannabis* flower were separated into two groups (10 grams a group) and placed on different racks within the pathogen reduction device. One 10 gram sample was placed on an industrial grade aluminum rack with air holes in order to maximize ozone flow and increase the surface area of the flower that would be exposed to ozone. A second 10 gram sample was place directly onto a rack screen (aluminum foil with holes pocked into it); however, because some of the homogenized *cannabis* flower was finer than the rack screen, some flower from the second 10 gram sample passed through the rack screen and landed on the lowest mesh screen in the device, thereby, creating a third sample for testing.

20 gram samples as described above were exposed to ozone for 0 minutes (control), 20 minutes, 30 minutes, 45 minutes, and 60 minutes at an ozone concentration of 200 ppm. Six 1 gram samples from each treatment time were processed and evaluated using a 3M® Petrifilm® Rapid Yeast and Mold Count Plate and accompanying Product Instructions. The ozone treated samples were homogenized, diluted with buffer (distilled water), and then 1 milliliter suspension samples were dispensed onto 3M® Petrifilm® Rapid Yeast and Mold Count Plates. The plates were incubated at 27° C. for greater than 60 hours in order to quantify the total yeast and mold remaining on the *cannabis* flower following exposure to ozone. Three of the six 1 gram samples were taken from the flower placed on the industrial grade aluminum rack as detailed above. Two of the 1 gram samples were taken from the flower placed directly on the screen. The final 1 gram sample was collected from the lowest mesh screen in the device where the finest flower collected after falling through the rack screen.

As detailed in the following Table 4 and Table 5, a 92% decrease in total yeast and mold bio-burden was observed after treatment with ozone, with Colony Forming Units (CFUs)/gram dropping from an average of 82,000 CFU/g to an average of 7,000 CFR/g after treatment with ozone for 60 minutes. The most significant reduction in CFU/g was observed in the first 20 minutes of exposure to ozone. After the first 20 minutes and up until 45 minutes, there was only an additional 1.1% reduction in CFU/g. However, between a 45 minute and 60 minute exposure to ozone, there was another 14.1% reduction in CFU/g. Notably, there was a reduction in yeast and mold across all 6 samples from roughly $10^5$ CFU/g to below 10,000 CFU/g following treatment with ozone in an embodiment of a disclosed pathogen reduction device.

TABLE 4

Average CFU/g of yeast and mold remaining on the tested *cannabis* flower following exposure to ozone for varying periods of time.

| Sample (exposure time in minutes) | Average CFU/g (all samples tested) |
| --- | --- |
| 0 minutes | 68,000 |
| 20 minutes | 18,000 |
| 30 minutes | 17,000 |
| 45 minutes | 16,000 |
| 60 minutes | 6,000 |

Table 4 reveals that fungi are strongly inhibited by ozone exposure. Notably, graphing the results of Table 4 (exposure time versus average CFU/g) allows an estimation of treatment time for sample with higher levels of fungal contamination than tested in Table 4. The data to support Table 4 is disclosed in Table 5.

TABLE 5

Results from experiments described above and presented in Table 4.

| Sample (6 samples for each exposure in minutes) | Location in Pathogen Reduction Device | CFU/g (Test 1) | CFU/g (Test 2) |
| --- | --- | --- | --- |
| T0-1 | Lowest mesh screen | 77,000 | 61,000 |
| T0-2 | Rack screen | 30,000 | 28,000 |
| T0-3 | Rack screen | 50,000 | 77,000 |
| T0-4 | Industrial grade aluminum rack | 25,000 | 53,000 |
| T0-5 | Industrial grade aluminum rack | 60,000 | 140,000 |
| T0-6 | Industrial grade aluminum rack | 82,000 | 130,000 |
| T20-1 | Lowest mesh screen | 18,000 | 24,000 |
| T20-2 | Rack screen | 15,000 | 16,000 |
| T20-3 | Rack screen | 15,000 | 17,000 |
| T20-4 | Industrial grade aluminum rack | 19,000 | 23,000 |
| T20-5 | Industrial grade aluminum rack | 12,000 | 18,000 |
| T20-6 | Industrial grade aluminum rack | 21,000 | 21,000 |
| T30-1 | Lowest mesh screen | 16,000 | 20,000 |
| T30-2 | Rack screen | 18,000 | 30,000 |
| T30-3 | Rack screen | 13,000 | 16,000 |
| T30-4 | Industrial grade aluminum rack | 16,000 | 15,000 |
| T30-5 | Industrial grade aluminum rack | 11,000 | 14,000 |
| T30-6 | Industrial grade aluminum rack | 20,000 | 20,000 |
| T45-1 | Lowest mesh screen | 7,100 | 11,000 |
| 45-2 | Rack screen | 13,000 | 15,000 |
| T45-3 | Rack screen | 11,000 | 12,000 |
| T45-4 | Industrial grade aluminum rack | 21,000 | 48,000 |
| T45-5 | Industrial grade aluminum rack | 16,000 | 17,000 |
| T45-6 | Industrial grade aluminum rack | 8,000 | 12,000 |
| T60-1 | Lowest mesh screen | 7,400 | 9,000 |
| T60-2 | Rack screen | 6,000 | 10,000 |
| T60-3 | Rack screen | 7,800 | 6,300 |
| T60-4 | Industrial grade aluminum rack | 770 | 3,100 |
| T60-5 | Industrial grade aluminum rack | 4,300 | 4,400 |
| T60-6 | Industrial grade aluminum rack | 6,300 | 7,100 |

T0-1 represents sample 1 with an ozone exposure time of 0 minutes.
T20-1 represents sample 1 with an ozone exposure time of 20 minutes.
T30-1 represents sample 1 with an ozone exposure time of 30 minutes.
T45-1 represents sample 1 with an ozone exposure time of 45 minutes.
T60-1 represents sample 1 with an ozone exposure time of 60 minutes.

Some additional ozone exposure tests were performed with *cannabis* flower or trim on a variety of commercially available strains using an embodiment of a disclosed pathogen reduction device. In each experiment (disclosed in Table 6) a reduction of mold and yeast CFU/g was measured (as disclosed above using 3M® Petrifilm® Rapid Yeast and Mold Count Plate and Product Instruction) after treating different weights of *cannabis* with an ozone concentration of 200 ppm for between 20 and 60 minutes.

TABLE 6

Results of ozone treatment of cannabis flower or trim to reduce mold and yeast. CFUs were measure before treatment (Initial CFU) and after treatment (Ending CUF) with ozone.

| Type of Product | Strain Type | Initial CFU | Ending CFU | Total Weight Run (lbs) | Ozone Concentration (ppm) | Length of Time (min.) |
| --- | --- | --- | --- | --- | --- | --- |
| Flower | Hybrid/Sativa | 100,000 | 5,400-5,500 | 1 lb | 200 | 20:00 |
| Flower | Hybrid/Indica | 51,750 | 30,000-32,000 | 6 lbs | 200 | 25:00 |
| Trim | Hybrid/Indica | 17,000 | 800-11,000 | 6 lbs | 200 | 25:00 |
| Flower | Hybrid/Indica | 2,200 | 220 | 1 lb | 200 | 45:00 |
| Flower | Indica | 320,000 | 91,000 | 3 lbs | 200 | 60:00 |

TABLE 6-continued

Results of ozone treatment of cannabis flower or trim to reduce mold and yeast. CFUs were measure before treatment (Initial CFU) and after treatment (Ending CUF) with ozone.

| Type of Product | Strain Type | Initial CFU | Ending CFU | Total Weight Run (lbs) | Ozone Concentration (ppm) | Length of Time (min.) |
|---|---|---|---|---|---|---|
| Trim | Hybrid/Sativa | 50,000 | 3,000 | 3 lbs | 200 | 60:00 |
| Flower | Hybrid/Indica | 110,000 | 3,000 | NA | 200 | 60:00 |
| Flower | Hybrid | 77,000 | 4500 | 5 lbs | 200 | 60:00 |

While ozone exposure can successfully reduce pesticides and fungus on *cannabis* flower, it has little to no effect on the terpenes of a *cannabis* flower. Cannabinoid and terpene content of *cannabis* flower was measured before exposure to 200 ppm of ozone in an embodiment of a disclosed pathogen reduction device and after a 60 minute exposure. The results are disclosed in Table 7 by the different cannabinoids and terpenes measured.

TABLE 7

A 60 minute exposure of cannabis flower to ozone had minimal to no effect on the cannabinoid and terpene content.

| Cannabinoid or Terpene | % Before Ozone Exposure (0 minutes) | % After Ozone Exposure (60 minutes) | % Change (decrease) |
|---|---|---|---|
| % THC | 0.749 | 0.680 | 9.2 |
| % THCA | 16.9 | 15.7 | 7.1 |
| % CBDA | 0.037 | 0.035 | 5.4 |
| % CBCA | 0.105 | 0.102 | 0.28 |
| % CBGA | 0.638 | 0.552 | 13.4 |
| % CBNA | 0.046 | 0.0458 | 0.04 |
| % THCVA | 0.077 | 0.076 | 1.2 |
| Total Terpene % | 2.11 | 1.94 | 8.1 |

Although specific examples were described herein, the scope of the technology is not limited to those specific examples. One skilled in the art will recognize other aspects, examples or improvements that are within the scope and spirit of the present technology. Therefore, the specific structure, acts, or media are disclosed only as illustrative examples according to the disclosure.

The invention claimed is:

1. A method for reducing the microbial count of plant pathogens in a sample of *cannabis* flower, comprising the steps of:
   a. obtaining a pathogen reduction device comprising, (i) a controller; and (ii) an ozone system including an ozone generator, an ozone chamber and an oxygen concentrator;
   b. placing a sample of *cannabis* flower comprising a plant pathogen in the ozone chamber;
   c. providing a preset concentration of ozone gas in the ozone chamber; and
   d. monitoring the concentration of ozone gas in the ozone chamber and automatically adjusting the concentration of ozone gas to a preset ozone concentration of from about 50 ppm to about 400 ppm, wherein when the sample of *cannabis* flower is exposed to ozone gas in the ozone chamber for a time period of from 1 minute to 48 hours the microbial count of plant pathogens in the sample of *cannabis* flower is reduced.

2. The method according to claim 1, wherein the oxygen concentrator is configured to concentrate oxygen from ambient air.

3. The method according to claim 2, wherein the sample of *cannabis* flower comprising a plant pathogen is exposed to ozone gas for a preset time period greater than 12 hours.

4. The method according to claim 2, wherein the sample of *cannabis* flower comprising a plant pathogen is exposed to ozone gas for a preset time period of 20 minutes to 90 minutes.

5. The method according to claim 4, wherein the sample is homogenized *cannabis* flower.

6. The method according to claim 4, wherein the sample of *cannabis* flower comprising a plant pathogen is placed in the ozone chamber for 20 minutes at an ozone concentration of about 200 ppm, and the method is effective to reduce the amount of *E. coli, Salmonella,* or *Listeria* in the sample by greater than 90%.

7. The method according to claim 4, wherein the preset concentration of gaseous ozone in the ozone chamber is maintained in the range of about 100 ppm to 300 ppm.

8. The method according to claim 7, wherein the preset concentration of gaseous ozone in the ozone chamber is maintained in the range of about 200 to 250 ppm.

9. The method according to claim 8, wherein the microbial count is total yeast and mold colony forming units (CFU), the total CFU in the sample of *cannabis* flower is approximately $10^5$ CFU/g, and after exposure to an ozone concentration of 200 ppm in the ozone chamber for 20 to 90 minutes, the method is effective to reduce the CFU to below 10,000 CFU/g.

10. The method according to claim 8, wherein the microbial count is total yeast and mold CFU, and the total CFU in the sample of *cannabis* flower is reduced by greater than 90% following exposure to an ozone concentration of 200 ppm in the ozone chamber for 60 minutes.

11. The method according to claim 8, wherein the microbial count is total yeast and mold CFU, and the method is effective to reduce the CFU in a sample of *cannabis* flower by 100,000 CFU, following exposure to an ozone concentration of 200 ppm in the ozone chamber for about 20 to 90 minutes.

12. The method according to claim 8, wherein the microbial count is total yeast and mold CFU, and the method is effective to reduce the microbial count by 50,000 CFU, following exposure to an ozone concentration of 200 ppm in the ozone chamber for about 20 to 90 minutes.

13. The method according to claim 8, wherein the THC and THCA levels in a sample of *cannabis* flower comprising a plant pathogen are substantially the same following exposure to an ozone concentration of about 200 ppm in the ozone chamber for about 20 to 90 minutes.

14. The method according to claim 8, wherein the terpene levels in a sample of *cannabis* flower comprising a plant pathogen are substantially the same following exposure to an ozone concentration of about 200 ppm in the ozone chamber for about 20 to 90 minutes.

15. A method for reducing the microbial count of plant pathogens in a *cannabis* sample, comprising the steps of:
   a. obtaining a pathogen reduction device comprising, (i) a controller; and (ii) an ozone system including an ozone generator, an ozone chamber and an oxygen concentrator;
   b. placing a *cannabis* sample comprising a plant pathogen in the ozone chamber;
   c. providing a preset concentration of ozone gas in the ozone chamber; and
   d. monitoring the concentration of ozone gas in the ozone chamber and automatically adjusting the concentration of ozone gas to a preset ozone concentration of from about 50 ppm to about 400 ppm, wherein when the *cannabis* sample is exposed to ozone gas in the ozone chamber for a time period of greater than one hour the microbial count of plant pathogens in the sample of *cannabis* flower is reduced.

16. The method according to claim 15, wherein the *cannabis* sample comprising a plant pathogen is exposed to ozone gas for a preset time period greater than 12 hours.

17. The method according to claim 16, wherein the *cannabis* sample comprising a plant pathogen is exposed to ozone gas for a preset time period of 12 hours to 16 hours.

18. The method according to claim 15, wherein the preset concentration of gaseous ozone in the ozone chamber is maintained in the range of about 100 ppm to 300 ppm.

19. The method according to claim 18, wherein the preset concentration of gaseous ozone in the ozone chamber is maintained in the range of about 150 ppm to 250 ppm.

20. The method according to claim 15, wherein the *cannabis* sample comprises *cannabis* flower.

* * * * *